United States Patent
Kantorovich et al.

(10) Patent No.: US 7,112,173 B1
(45) Date of Patent: Sep. 26, 2006

(54) DETERMINATION OF ACOUSTIC VELOCITY IN BONE

(75) Inventors: Edward Kantorovich, Rehovot (IL); Vladimir Pasternak, Bat-Yam (IL); Shai Ashkenazi, Rehovot (IL); Elena Ledenev, Rehovot (IL); Andrey Mordvinov, Ramla (IL); Yehuda Niv, Nes-Ziona (IL)

(73) Assignee: Sunlight Medical Ltd., Rehovot (IL)

( * ) Notice: Subject to any disclaimer, the term of this patent is extended or adjusted under 35 U.S.C. 154(b) by 0 days.

(21) Appl. No.: 09/623,288

(22) PCT Filed: Jun. 24, 1998

(86) PCT No.: PCT/IL98/00299

§ 371 (c)(1),
(2), (4) Date: Nov. 1, 2000

(87) PCT Pub. No.: WO99/45348

PCT Pub. Date: Sep. 10, 1999

Related U.S. Application Data

(60) Provisional application No. 60/076,698, filed on Mar. 3, 1998.

(51) Int. Cl.
*A61B 8/02* (2006.01)

(52) U.S. Cl. .................. 600/449; 600/438
(58) Field of Classification Search .......... 600/437, 600/439, 449; 73/597, 599, 602
See application file for complete search history.

(56) References Cited

U.S. PATENT DOCUMENTS

| | | | |
|---|---|---|---|
| 3,127,950 A | 4/1964 | Itria | |
| 3,228,232 A | 1/1966 | Proctor | |
| 3,288,241 A | 11/1966 | Bancroft et al. | |
| 3,372,163 A | 3/1968 | Tessandori | |
| 3,512,400 A | 5/1970 | Lynnworth | |
| 3,720,098 A | 3/1973 | Dixon | |
| 3,847,141 A | 11/1974 | Hoop | |
| 4,083,232 A | 4/1978 | Heyser et al. | |

(Continued)

FOREIGN PATENT DOCUMENTS

EP   0 797 952   10/1997

(Continued)

OTHER PUBLICATIONS

Heany, R. P. et al.; "Osteoporotic Bone Fragility Detection by Ultrasound Transmission Velocity"; JAMA—The Journal of the American Medical Association; vol. 261; No. 20; May 26, 1989; pp. 2986-2990; XP000618753.

(Continued)

*Primary Examiner*—Francis J. Jaworski
(74) *Attorney, Agent, or Firm*—Kenyon & Kenyon LLP

(57) ABSTRACT

A method for determining an acoustic velocity in a segment of a bone covered with a layer of soft tissue having an outer surface, which includes determining a first travel time of a first ultrasonic wave along a first path from the outer surface back to the outer surface which path includes at least a first part of the bone segment together with determining a second travel time of a second ultrasonic wave along a second path from the outer surface back to the outer surface, which path includes at least a second part of the bone segment and also determining a third travel time of a third ultrasonic wave along a third path from the outer surface back to the outer surface which path includes at least a third part of the bone segment, and deriving the acoustic velocity in the segment of bone from the three determined travel times.

37 Claims, 9 Drawing Sheets

U.S. PATENT DOCUMENTS

| | | | |
|---|---|---|---|
| 4,361,154 A | 11/1982 | Pratt, Jr. | |
| 4,421,119 A | 12/1983 | Pratt, Jr. | |
| 4,442,713 A * | 4/1984 | Wilson et al. | 73/599 |
| 4,597,292 A | 7/1986 | Fujii | |
| 4,640,132 A | 2/1987 | Flora | |
| 4,669,482 A | 6/1987 | Ophir | |
| 4,752,917 A | 6/1988 | Dechape | |
| 4,774,959 A | 10/1988 | Palmer et al. | |
| 4,913,157 A * | 4/1990 | Pratt et al. | 600/449 |
| 4,926,870 A | 5/1990 | Brandenburger | |
| 4,930,511 A | 6/1990 | Rossman et al. | |
| 4,941,474 A | 7/1990 | Pratt, Jr. | |
| 5,038,787 A | 8/1991 | Antich et al. | |
| 5,143,069 A | 9/1992 | Kwon et al. | |
| 5,143,072 A | 9/1992 | Kantorovich et al. | |
| 5,197,475 A | 3/1993 | Antich et al. | |
| 5,235,981 A | 8/1993 | Hascoet et al. | |
| 5,396,891 A | 3/1995 | Whitney et al. | |
| 5,426,979 A | 6/1995 | Kantorovich et al. | |
| 5,720,290 A | 2/1998 | Buhler et al. | |
| 6,221,019 B1 * | 4/2001 | Kantorovich | 600/449 |

FOREIGN PATENT DOCUMENTS

| | | |
|---|---|---|
| SU | 1159556 | 6/1985 |
| SU | 1172534 | 8/1985 |
| SU | 1175435 | 8/1985 |
| WO | WO 91/14400 | 10/1991 |
| WO | WO 97/13145 | 4/1997 |

OTHER PUBLICATIONS

Piletskas, E. L.; "Database WPI"; Section PQ; Week 8749; Derwent Publications Ltd.; AN 87-347489; XP002085199; and SU 1 308 319 A; May 7, 1987.

Shmakov, Y. E.; "Database WPI"; Section PQ; Week 8909; Derwent Publications Ltd.; AN89-067923; XP002085200; and SU 1 420 383 A; Aug. 30, 1988.

Kolsky et al., "Propagation in Bounded Elastic Media", 1953, *Stress Waves in Solids*, pgs. 80-83, Oxford and Clarendon Press.

Hastings et al.., "Inspection, Processing and Manufacturing Control of Metal by Ultrasonic Methods", Jun. 28, 1949, Symposium on Ultrasonic Testing, 52$^{nd}$ Annual Meeting of the American Society for Testing Materials, pgs. 14-47.

Graff, K.F., "Wave Motion in Elastic Solids", 1975, Clarendon Press, Oxford, England, pg. 326.

Greenfield et al., "Measurement of the Velocity of Ultrasound in Human Cortical Bone In Vivo", Mar. 1981, Radiology, vol. 138, pgs. 701-710.

McCartney et al., "Combined 2.25 MHz Ultrasound Velocity and Bone Mineral Density Measurements in the Equine Metacarpus and Their In Vivo Applications", Nov. 1987, Medical and Biological Engineering and Computation, vol. 25, pgs. 620-626.

\* cited by examiner

DETERMINATION OF ACOUSTIC VELOCITY IN BONE

This application is a 371 of PCT/IL98/00299 filed Jun. 24, 1998, which application is a US national filing of PCT Application PCT/IL98/00299, filed Jun. 24, 1998, and claims the benefit of U.S. Provisional patent application No. 60/076,698, filed Mar. 3, 1998, the disclosure of which is incorporated herein by reference.

FIELD OF THE INVENTION

The present invention relates to non-invasive measurement of the mechanical properties of bone and especially to measurement at arbitrary angles relative to the bone.

BACKGROUND OF THE INVENTION

It is known in the art that the velocity of a sound wave in a material depends on the mechanical properties of the material.

A sound wave that reaches a solid at an angle will typically propagate through and along the solid as a combination of three waves, namely, longitudinal, transverse and surface waves, wherein each wave has a different velocity. In bone velocity determination, the longitudinal wave, which is the fastest, is usually measured. The velocity of the longitudinal wave is:

$$V_L = \sqrt{\frac{E(1-\sigma)}{\rho(1+\sigma)(1-2\sigma)}} \quad (1)$$

where E, $\sigma$ and $\rho$ are, respectively, the Young's Modulus, the Poisson's ratio of lateral contraction to longitudinal extension and the mass density of the material.

In an article entitled, "Osteoporotic Bone Fragility: Detection by Ultrasound Transmission Velocity," R. P. Heaney et al., *JAMA*, Vol. 261, No. 20, May 26, 1989, pp. 2986–2990, the Young's Modulus of bone, E, is given empirically as:

$$E=K\rho^2 \quad (2)$$

The velocity of the longitudinal sound wave in the bone is then:

$$V_L=\sqrt{(E/\rho)}=\sqrt{(K\rho)} \quad (3)$$

where K is a constant which incorporates a number of factors, such as spatial orientation of the bone structures, inherent properties of the bone material and fatigue damage. Thus, the velocity of a longitudinal wave is a function of the mass density and can be used as an indicator of the quality of bone.

In order to perform in vivo ultrasonic measurements of the mechanical properties of bone, it is necessary to transmit an ultrasonic wave through the soft tissue surrounding the bone. Unfortunately, the thickness of the soft tissue varies along the length of the bone. Also, the soft tissue velocity is not a constant value for all soft tissues. These variations can affect the accuracy of the ultrasound propagation time measurement through the bone. Typically, the variations in thickness of the soft tissue and its velocity are either ignored or an attempt is made to cancel the effects of the soft tissue.

U.S. Pat. No. 5,143,072, the disclosure of which is incorporated herein by reference, describes a method of overcoming the effects of the unknown thickness of the intervening soft tissue, by ensuring that the measurements will be taken when the portion of the path which passes through soft tissue is of a same length for different measurements. A transmitter and two receivers are placed in a collinear configuration parallel to the bone. When a wave is transmitted from the transmitter towards the bone, the wave passes through intervening soft tissue and then travels along the bone. The two receivers detect ultrasonic waves that exit the bone and travel back through soft tissue to the two receivers. Ignoring the soft tissue, the difference between the path from the transmitter to the first receiver and to the second receiver is a segment of bone whose length is the same as the distance between the two receivers. Generally, the soft tissue cannot be ignored. However, if the two receivers are rather close together, the length of the paths in the soft tissue, between the bone and the receivers, will be approximately the same and should, to a certain level of precision, cancel out. In one embodiment described in the above patent document, the receiver/transmitter configuration is rocked and the measurements are taken only when the (shortest) distances between the bone and the two receivers are the same. These distances may be measured using the receivers as transmitter/receivers that bounce a wave off the bone. When the propagation times are equal, the configuration is assumed to be collinear with the bone.

However, even this method has several shortcomings. First, soft tissue velocity is not a constant, rather, it varies with the type of soft tissue. In addition, the propagation paths between the bone and the receivers are not the same for the reflected wave and for the wave from the transmitter, so the calculated acoustic bone velocity may not be correct. Second, the above-described method requires a relatively long portion of flat bone. Thus, only a small number of bones can be tested, using this method, such as the tibia. In addition, since high frequency ultrasonic waves are very lossy, it is not practical to use them for this method.

PCT publication WO 97/13145, the disclosure of which is incorporated herein by reference, describes an alternative method of bone velocity determination, in which a velocity in a significantly shorter portion of bone may be measured. In this publication, several waves are transmitted to the bone and received by one or more receivers. One of the waves travels through both bone and soft tissue and one or more waves travel only through soft tissue. The waves that travel only through soft tissue are used to calculate the soft tissue velocity. The calculated soft tissue velocity is applied to extract the bone velocity from the travel time of the wave that travels through both bone and soft tissue.

SUMMARY OF THE INVENTION

It is one of the objects of some embodiments of the present invention to provide a method of acoustic bone velocity determination having a high spatial resolution. In addition, in some preferred embodiments of the invention a small portion of bone can be measured, so that almost all the bones of the human body can be measured.

Another object of some preferred embodiments of the invention is to provide a method of acoustic bone velocity determination even when a measuring probe is not parallel to the bone. It should be appreciated that in many medical situations, as opposed to non-destructive testing situations, the relative layout of the bone and the skin cannot be accurately determined in a simple manner. In non-destructive testing situation, on the other hand, any intervening layer is usually manufactured to a known thickness.

Another object of some preferred embodiments of the invention is to provide a method of acoustic bone velocity determination where the bone is not smooth and/or where the bone presents a curved or otherwise non-planar surface to a measurement probe.

Another object of some preferred embodiments of the invention is to provide a measurement probe and/or a measurement method in which there is a minimum amount of interference between transmitting elements and receiving elements.

One aspect of some preferred embodiments of the invention relates to acquiring several measurements of the travel time of an ultrasonic wave, along two or more different paths between one or more transmitters and one or more receivers. In a preferred embodiment of the invention, at least three and preferably all the paths include a section of bone whose acoustic velocity is to be determined.

Another aspect of some preferred embodiments of the invention relates to the amount of overlap between paths along which ultrasonic waves travels as a part of measuring the ultrasonic velocity. In a preferred embodiment of the invention, the bone sections of the different paths do not substantially overlap. Additionally or alternatively, the paths of the ultrasonic waves in soft tissue surrounding the bone do not substantially overlap.

Another aspect of some preferred embodiments of the invention relates to the relative alignments of transmitters and receivers used to determine travel times for ultrasonic waves. In a preferred embodiment of the invention, not all of the transmitters and/or receivers are collinear. In a preferred embodiment of the invention, the transmitters and/or receivers are not all coplanar. Alternatively or additionally, the transmitters and receivers used may be arranged in any order, for example, one order is a transmitter, a receiver, a transmitter and a receiver. Alternatively or additionally, a single ultrasonic element may function both as a transmitter and as a receiver.

Another aspect of some preferred embodiments of the invention relates to a method of solving equations which links measured values and unknown variables. In a preferred embodiment of the invention, the acoustic bone velocity is determined by solving a set of simultaneous equations, into which measurement times are inserted. Additionally or alternatively, the simultaneous equations are analytically simplified so that only one equation, containing only one variable, for example the bone velocity, remains.

Another aspect of some preferred embodiments of the invention relates to being able to perform several levels of estimation of a determined variable, by making different assumptions about other unknowns. In a preferred embodiment of the invention, at least four variables are interrelated: bone velocity, soft tissue velocity, an average distance of probe from bone and an angle between the probe and the bone. In a preferred embodiment of the invention, any one of these variables may be estimated or be calculated from the other variables by solving a set of equations. In a preferred embodiment of the invention, the soft tissue velocity is estimated, for example to be 1500 m/s, so only three variables need to be calculated. Thus, only three travel time measurements are necessary. Additionally or alternatively, more than four variables may be interrelated, for example, if the soft tissue is assumed to contain two layers, each with a different acoustic velocity. Additionally or alternatively, a known or assumed "bone" acoustic velocity may be used to determine a distance between a transmitter and a receiver and/or other dimensions of a probe, during a calibration stage with a phantom having known characteristics.

Another aspect of some preferred embodiments of the invention relates to a method of determining travel time of an acoustic wave along a desired path. In some preferred embodiments of the invention, a travel time between a transmitter and a receiver are determined by detecting a first wave arriving at a receiver from the transmitter. In some cases however, that first wave may not have traveled along a desired path. In a preferred embodiment of the invention, a wave is determined to have traveled along a desired path based on characteristics of the detected wave. In one example, a spectra of a wave is different depending on whether it traveled through bone or not. In a preferred embodiment of the invention, the spectra is different due to frequency-attenuation relationships and/or frequency-dispersion relationships being dependent on the material through which the wave travels. Additionally or alternatively, if two waves arrive at a receiver, along two different paths, an increase in wave amplitude, at least for some frequency components, may be expected when the two wave arrive overlapping in time at the receiver. In a preferred embodiment of the invention, instead of predetermining such special characteristics of a wave, the time of arrival of a desired wave at a receiver is determined by performing a temporal correlation of waves at two receivers which detect a similarly characterized wave.

Another aspect of some preferred embodiments of the invention relates to reducing interference caused by cross talk between ultrasonic elements of a receiver/transmitter probe, especially for acoustic bone and/or soft tissue velocity determination. In a preferred embodiment of the invention, the probe design presents a labyrinth to waves which travel through the probe, between ultrasonic elements of the probe. Thus, such wave may be delayed. Additionally or alternatively, spaces between such ultrasonic elements are filled with acoustically slow materials and/or acoustically attenuating materials. This velocity reduction allows for time gating out the waves which travel through the probe. Additionally or alternatively, electrical shielding is provided to shield receivers from transmitters. This reduces electrical cross-talk.

In a preferred embodiment of the invention, an acoustic chamber between the ultrasonic elements and the body to be measured is formed of attenuating materials to reduce cross-talk between the ultrasonic elements. Alternatively or additionally, the chamber is filled with acoustically slow materials.

Alternatively or additionally, when an ultrasonic probe is placed against a human subject an attenuating and/or low acoustical velocity coupling material is used, to delay and/or attenuate undesirable cross-talk.

Another aspect of some preferred embodiments of the invention relates to defining a detection window having a late cutoff time additionally or alternatively an early cutoff time. In a preferred embodiment of the invention, such late and/or early cutoff times are defined so that ultrasonic waves which do not pass through the bone cannot arrive at the receiver within the time window. Alternatively or additionally, such waves may arrive, but only at an extremely attenuated amplitude. In a preferred embodiment of the invention, the cutoff time or times for each probe, are stored on a storage media associated with the probe. In a preferred embodiment of the invention, the storage media is packaged with the probe. Alternatively or additionally, the storage media is physically attached to or mounted on the probe. Additionally or alternatively to time windows, other calibration information and/or frequency characteristics information, especially for discriminating waves which travel through bone, and/or characteristics of the probe and/or identification information and/or usage information for the probe are stored on the storage media. In a preferred embodiment of the invention, the storage media comprises an electronic circuit embedded in the probe. Preferably, the circuit comprises an EPROM. In a preferred embodiment of the invention, the circuit is interrogated when the probe is connected into an parent device, which parent device preferably comprises circuitry for driving the probe and/or determining an acoustic velocity based on waves arriving from the probe.

There is thus provided in accordance with a preferred embodiment of the invention, a method of determining an acoustic velocity in a segment of a bone covered with a layer of soft tissue having an outer surface, comprising:

determining a first travel time of a first ultrasonic wave along a first path from said outer surface back to said outer surface which path includes at least a first part of said bone segment;

determining a second travel time of a second ultrasonic wave along a second path from said outer surface back to said outer surface which path includes at least a second part of said bone segment;

determining a third travel time of a third ultrasonic wave along a third path from said outer surface back to said outer surface which path includes at least a third part of said bone segment; and deriving said acoustic velocity in said segment of bone from said three determined travel times.

Preferably, at least two of said first, second and third waves are generated simultaneously by a single transmitter.

Alternatively or additionally, at least two of said first, second and third waves are detected simultaneously by a single receiver. Alternatively or additionally, at least two of said first, second and third waves each have an average frequency that is substantially the same, when generated.

In a preferred embodiment of the invention, at least two of said first, second and third waves each have an average frequency that is substantially different, when generated. Alternatively or additionally, at least two of said first, second and third waves each have an average frequency that is substantially different, when detected.

Alternatively or additionally, at least two of said first, second and third waves each have an average frequency that is substantially the same, when detected.

In a preferred embodiment of the invention, each of said first, second and third paths comprises soft tissue portions and wherein at least two of said first, second and third paths have an overlap of at least 20% over the length of their soft tissue portions.

Alternatively or additionally, each of said first, second and third paths comprises soft tissue portions and wherein at least two of said first, second and third paths have an overlap of at least 30% over the length of their soft tissue portions.

Alternatively, each of said first, second and third paths comprises soft tissue portions and wherein no two of said first, second and third paths overlap by more than 20% of the length of their soft tissue portions.

Alternatively or additionally, each of said first, second and third paths comprises soft tissue portions and wherein no two of said first, second and third paths overlap by more than 30% of the length of their soft tissue portions.

In a preferred embodiment of the invention, at least two of said first, second and third bone parts overlap at least 20% over their length.

In a preferred embodiment of the invention, at least two of said first, second and third bone parts overlap at least 40% over their length.

Alternatively or additionally, at least two of said first, second and third bone parts overlap at least 70% over their length. Alternatively no two of said first, second and third bone parts overlap by 20% or more of their length.

In a preferred embodiment of the invention, no two of said first, second and third bone parts overlap by 40% or more of their length. In a preferred embodiment of the invention, no two of said first, second and third bone parts overlap by 70% or more of their length.

In a preferred embodiment of the invention, the method comprises estimating a soft tissue velocity and wherein deriving said acoustic velocity comprises deriving said bone velocity using said estimated soft tissue velocity. Alternatively, the method comprises determining a fourth travel time of a fourth ultrasonic wave along a fourth path from said outer surface back to said outer surface which path includes at least a fourth part of said bone segment and wherein deriving said acoustic velocity comprises deriving a bone velocity also using the fourth travel time.

In a preferred embodiment of the invention, geometric projections of at least two of said acoustic wave paths onto the outer surface are parallel. Alternatively no geometric projections of said acoustic wave paths onto the outer surface are parallel to each other. Alternatively, said acoustic waves are generated and detected by ultrasonic elements and wherein said ultrasonic elements are not coplanar.

In a preferred embodiment of the invention, said outer surface is not parallel to an outer surface of said bone, while said waves travel through said bone. Alternatively or additionally, deriving comprises solving a set of simultaneous equations.

In a preferred embodiment of the invention, the method comprises repeating said determining of travel times and said deriving of acoustic velocity for a plurality of bone segments, to generate a map of acoustic bone velocity of at least a portion of a bone. Alternatively or additionally, the method comprises repeating said determining of travel times and said deriving of acoustic velocity for a plurality of orientations of travel of said waves through said bone, to generate a map of directional acoustic bone velocity of at least a portion of a bone.

There is also provided in accordance with a preferred embodiment of the invention, a method of determining at least one of a set of unknowns, including an acoustic bone velocity, soft tissue velocity, a thickness of said soft tissue and an inclination angle of an outer surface of said soft tissue relative to the bone, comprising:

determining the travel time of at least three ultrasonic waves which travel from said surface, to said bone, along the surface of said bone and back to said surface; and deriving at least one of said unknowns from said three determined travel times.

Preferably, said at least one unknown comprises the soft tissue velocity. Alternatively, the method comprises assuming a value for at least one of said unknowns. Preferably, said assumed unknown comprises a soft tissue velocity.

There is also provided in accordance with a preferred embodiment of the invention, a probe for acoustic bone velocity measurement, comprising:

at least four ultrasonic elements, at least one of which comprises a transmitter and at least one of which comprises a receiver; and a controller which controls said at least one transmitter to transmit at least three ultrasonic waves through a layer of soft tissue to a bone, which controller detects via said at least one receiver, at least relative travel times of said three waves, after they travel along a surface of said bone and which controller derives an acoustic bone velocity from said determined at least travel times.

Preferably, said at least four ultrasonic elements comprise three transmitters and one receiver. Alternatively, said at least four ultrasonic elements comprise three receivers and one transmitter. Alternatively, said at least four ultrasonic elements comprise two receivers and two transmitters.

In a preferred embodiment of the invention, said ultrasonic elements are not all collinear. Alternatively, said ultrasonic elements are all collinear. Alternatively or additionally, all of said ultrasonic elements are coplanar. Alternatively or additionally, not all of said ultrasonic elements are coplanar.

Alternatively or additionally, said probe is adapted to be urged against a skin layer of a soft tissue and wherein said ultrasonic elements are inclined relative to said layer at an inclination angle. Preferably, said inclination angle is determined responsive to an expected acoustic bone velocity.

In a preferred embodiment of the invention, said at least three ultrasonic waves are generated by a single transmitter as a single wave, which wave scatters to form said at least three waves.

There is also provided in accordance with a preferred embodiment of the invention, a probe for acoustic velocity determination, comprising:

at least two ultrasonic elements, at least one of which comprises a transmitter and at least one of which comprises a receiver; and a plurality of staggered acoustic barriers which significantly attenuate ultrasonic waves which travel along a direct line in said probe between said transmitter and said receiver.

Preferably, volumes in said probe between said at least one transmitter, said at least one receiver and said barriers comprise an ultrasonic attenuating filler. Alternatively or additionally, said probe comprises electrical shielding for said at least one receiver and at least one transmitter. Alternatively or additionally, said probe comprises at least two additional ultrasonic elements, which elements are also acoustically separated by said barriers.

In a preferred embodiment of the invention, said probe is adapted for acoustic bone velocity determination;

In a preferred embodiment of the invention, an acoustic chamber is defined as being bordered by said at least transmitter and said at least receiver and a plane to be placed against a body, wherein said acoustic chamber comprises acoustically attenuating material.

There is also provided in accordance with a preferred embodiment of the invention, an ultrasonic probe comprising:

at least two ultrasonic elements, at least one of which comprises a transmitter and at least one of which comprises a receiver; and an acoustic chamber defined as being bordered by said at least transmitter and said at least receiver and a plane to be placed against a body, wherein said acoustic chamber comprises acoustically attenuating material.

In a preferred embodiment of the invention, ultrasonic elements in an ultrasonic velocity determination probe are comprised in an ultrasonic element grid.

Preferably, said probe scans a bone by electrically scanning said grid. Alternatively or additionally, at least one of said ultrasonic elements comprises a phased array. Preferably, an inclination angle for said phased array elements is achieved by electrically controlling said phased array.

Alternatively or additionally, said probe comprises a memory device attached to said probe, wherein calibration data for said probe are stored on said memory device. Preferably, said calibration data comprises at least one distance between ultrasonic elements. Alternatively or additionally, said calibration data comprises at least one vertical displacement of an ultrasonic element. Alternatively or additionally, said calibration data comprises at least one vertical displacement of a path between two of said ultrasonic elements. Alternatively or additionally, said calibration data comprises a late cutoff time, after which received waves are ignored. Alternatively or additionally, said calibration data comprises an acoustic velocity of a portion of the probe between at least one of said ultrasonic elements and a surface against which said probe is urged in use.

There is also provided in accordance with a preferred embodiment of the invention, a method of rejecting parasitic signals in an acoustic bone velocity probe, comprising:

detecting signals arriving at a receiver, from a transmitter, ostensibly after the signal traveled through a portion of bone; and rejecting said signal if said signal arrives after a predetermined time limit, associated with waves which do not travel through the bone.

Preferably, said signal is rejected if it arrives before a second time limit. Alternatively or additionally, said predetermined time limit is determined based on a calibration of the probe.

There is also provided in accordance with a preferred embodiment of the invention, a method of detecting the arrival of an ultrasonic wave from a bone, in the presence of waves traveling substantially only through soft tissue, comprising:

acquiring a signal representative of said bone wave and said soft-tissue waves; and analyzing said signals to detect changes in amplitude in at least one frequency in said signal, which changes are associated with said wave from said bone.

Preferably, said analyzing comprises determining a significant increase in amplitude of the signal, when a wave arrives from a bone.

There is also provided in accordance with a preferred embodiment of the invention, a method of detecting the arrival of an ultrasonic wave from a bone, in the presence of waves traveling substantially only through soft tissue, comprising:

acquiring a signal representative of said bone wave and said soft tissue waves at a first receiver;

acquiring a signal representative of said bone wave and said soft tissue waves at a second receiver; and correlating the two signal to detect arrival of a wave from said bone. Preferably, said correlation is performed responsive to the generation of said wave. Preferably, said correlation is performed responsive to an expected arrival time window of said wave.

There is also provided in accordance with a preferred embodiment of the invention, a method of acoustic bone velocity determination, comprising:

urging an acoustic bone velocity probe onto the surface of a soft tissue layer and not parallel to an underlying bone surface;

transmitting at least one wave to said bone surface and receiving at least two waves from said bone surface, wherein said received waves are waves that are not reflected from said surface;

measuring a travel time for each of said received waves; and deriving said acoustic bone velocity from said measured travel times.

There is also provided in accordance with a preferred embodiment of the invention, a method of acoustic bone velocity determination, comprising:

urging an acoustic bone velocity probe onto the surface of a soft tissue layer and not parallel to an underlying bone surface;

transmitting at least one wave from said probe to said bone surface and receiving at least two waves from said bone surface, wherein waves are transmitted and received from locations in the probe, which transmission and reception locations are not coplanar;

measuring a travel time for each of said received waves; and deriving said acoustic bone velocity from said measured travel times.

There is also provided in accordance with a preferred embodiment of the invention, a method of acoustic bone velocity determination, comprising:

urging an acoustic bone velocity probe onto the surface of a soft tissue layer and not parallel to an underlying bone surface;

transmitting at least one wave to said bone surface and receiving at least two waves from said bone surface, wherein the waves connect at least three locations in the probe, each said location being a transmission location or a receiving location and wherein at least one pair of connected locations is not collinear with any other pair of connected locations;

measuring a travel time for said received waves; and deriving said acoustic bone velocity from said measurements.

There is also provided in accordance with a preferred embodiment of the invention, a method of acoustic bone velocity determination, comprising:

transmitting at least one ultrasonic wave to a bone, which wave travels along the surface of the bone;

receiving said wave; and analyzing a travel time of a particular frequency in said received wave, wherein said particular frequency is related to an expected thickness of a cortex of the bone.

Preferably, said wave is transmitted as a narrow band wave at said particular frequency.

There is also provided in accordance with a preferred embodiment of the invention, a method of calibrating a probe including a plurality of ultrasonic elements including at least one transmitter and one receiver, comprising:

coupling said probe to a plate having a first known acoustic velocity and measuring a first plurality of travel times between at least two pairs of said ultrasonic elements;

coupling said probe to a plate having a second known acoustic velocity and measuring a second plurality of travel times between at least two pairs of said ultrasonic elements; and determining from said travel times at least two distances between pairs of said ultrasonic elements.

Preferably, determining comprises determining at least one average vertical displacement of at least one of said pairs of elements.

There is also provided in accordance with a preferred embodiment of the invention, a method of calibrating a probe comprising a plurality of ultrasonic elements including at least one transmitter and one receiver, the method comprising:

coupling said probe to a plate having a first known acoustic velocity and measuring a first plurality of travel times between at least two pairs of said ultrasonic elements;

coupling said probe to a plate having a second known acoustic velocity and measuring a second plurality of travel times between at least two pairs of said ultrasonic elements; and determining from said travel times at least one average vertical displacement of at least one of said pairs of elements.

In a preferred embodiment of the invention, said plurality of ultrasonic elements comprises at least four ultrasonic elements.

There is also provided in accordance with a preferred embodiment of the invention, a probe for acoustic bone velocity determination, comprising:

at least two ultrasonic elements, at least one of which comprises a transmitter and at least one of which comprises a receiver; and a memory device attached to said probe, wherein calibration data for said probe are stored on said memory device, wherein said calibration data comprises at least one vertical displacement of a path between two of said ultrasonic elements.

There is also provided in accordance with a preferred embodiment of the invention, a probe for acoustic bone velocity determination, comprising:

at least two ultrasonic elements, at least one of which comprises a transmitter and at least one of which comprises a receiver; and a memory device attached to said probe, wherein calibration data for said probe are stored on said memory device, wherein said calibration data comprises a late cutoff time, after which received waves are ignored.

In a preferred embodiment of the invention, said calibration data comprises at least one distance between ultrasonic elements. Alternatively or additionally, said calibration data comprises at least one vertical displacement of an ultrasonic element. Alternatively or additionally, said calibration data comprises an acoustic velocity of a portion of the probe between at least one of said ultrasonic elements and a surface against which said probe is urged in use.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same or similar numeral in all the figures in which they appear, in which:

FIG. 12 is a partial schematic view of a cut human bone; and.

DETAILED DESCRIPTION OF PREFERRED EMBODIMENTS

Figure 1:
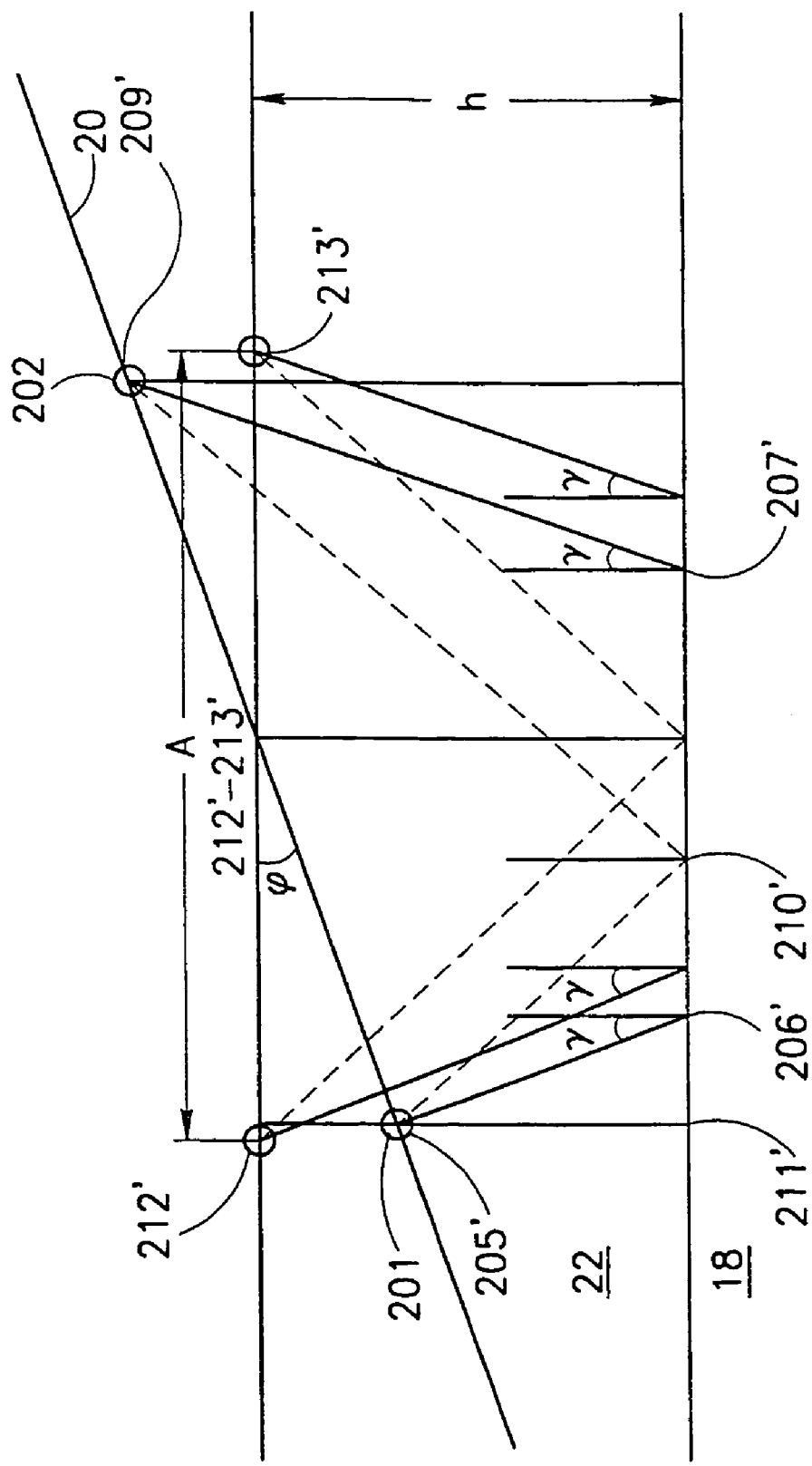
FIG. 1 illustrates schematically various variables of an acoustic velocity determination measurement, in accordance with a preferred embodiment of the invention.

FIG. 1 illustrates a simplified situation in which an acoustic bone velocity of a bone 18 is to be measured through an intervening soft tissue layer 22. An ultrasonic wave is generated by an ultrasonic element 201 (a transmitter) and detected by an ultrasonic element 202 (a receiver). There are many paths that the ultrasonic wave can and does take between the two ultrasonic elements. However, each path has different attributes. In particular, one path is the fastest path. In a preferred embodiment of the invention, the fastest path includes a bone segment.

$\phi$ is defined as the angle between the line connecting the two ultrasonic elements and a line parallel to the surface of bone 18. h is defined as the average distance between the ultrasonic elements and bone 18. A skin 20, which defines the surface of soft tissue 22 is usually flush with probe 250. Considering the configuration in which $\phi \neq 0$, elements 201 and 202 are situated at positions 205' and 209' respectively, the three main paths (for a longitudinal wave) are:

(a) a direct path along the surface of soft tissue 22, from element 201 to element 202.

(b) a path in which a wave is reflected off bone 18 at a position 210'.

(c) a path which travels through soft tissue from position 205' to a first position 206' on bone 18, enters bone 18 at position 206', travels along the upper layer of bone 18 to a second position 207' and then exits the bone and travels through the soft tissue to position 209'.

A. Acoustic Wave Propagation Only via Surface of Soft Tissue

This wave travels through soft tissue 22 from transmitter position 205' to receiver position 209' along a surface layer of the soft tissue 22. In many cases, the wave will actually travel along skin 20 and/or along acoustic grease which may be used to couple the ultrasonic elements to soft tissue 22. The acoustic wave travels through soft tissue 22 at a soft tissue acoustic velocity $V_S$, which is approximately 1540 m/s.

The acoustic propagation time of a wave traveling from transmitter 201 to receiver 202 is determined by the following expression:

$$T_{205'-209'} = \frac{A_{205'-209'}}{V_S}, \quad (4)$$

where $A_{205'-209'}$ is a distance between transmitter 201 and receiver 202.

B. Acoustic Wave Propagation from Transmitter to Receiver by Reflection from Bone This wave travels from transmitter position 205', through soft tissue 22, is reflected from the surface of bone 18 at a reflection position 210' to reach receiver 202 at receiver position 209'.

The propagation time for this wave is determined using by following expression:

$$T_{205'-210'-209'} = \frac{A_{205'-210'-209'}}{V_S}, \quad (5)$$

where $A_{205'-210'-209'}$ is the length of a path from position 205' to reflected position 210', and then to receiver position 209'. The distance $A_{205'-210'-209'}$, depends on the thickness h of soft tissue 22 and angle φ. Since the path is longer than the direct path described in "A", if the soft tissue velocity is the same for both paths, then $T_{205'-210'-209'} > T_{205'-209'}$.

C. Acoustic Wave Propagation from Transmitter, Through Soft Tissue, Along the Surface of Bone and to Receiver A Critical angle γ is defined by a ratio between the soft tissue acoustic velocity $V_S$ and a bone acoustic velocity $V_B$:

$$\sin\gamma = \frac{V_S}{V_B}, \quad (6)$$

where $V_B > V_S$.

This wave travels through soft tissue 22 from transmitter position 205' to reach first position 206' at the surface of bone 18; the wave then enters bone 18 at a first angle with respect to a perpendicular line to the surface of the bone 18, propagates along the surface of the bone 18 from first position 206' to second position 207', exits bone 18 at a second angle and then travels through the soft tissue 22 until it reaches receiver position 209'.

As is well known in optics, the fastest path between positions 205' and 209' and which includes the bone determines the first and second angles to be the critical angle. If no such path exists, a path of type B will be faster. It should be appreciated that even though paths of type A may theoretically be faster than paths of type C, if the ultrasonic wave is transmitted as a focused beam, substantially all the energy of the beam will be directed at the bone.

The travel time for a wave of type C may be determined using either of two methods. First, the duration of the travel may be measured, under circumstances described below where it can be assured that the detected wave is a type C wave and not a type B or type A wave. Alternatively, the travel time may be calculated as a function of other defined or derived variables. It is useful to breakdown the travel time into components:

$T_{205'-206'}$—the time that the wave travels (in soft tissue 22) from transmitter position 205' to position 206';

$T_{206'-207'}$—the time that the wave travels along the surface of bone 18 from position 206' to position 207'; and $T_{207'-209'}$—the time that the wave travels (in soft tissue 22) from position 207' to receiver position 209'.

Thus, the total travel time is:

$$T_{total} = T_{205'-206'} + T_{206'-207'} + T_{207'-209'}. \quad (7)$$

The projection of path 205'-206'-207'-209' onto a line parallel to bone 18, is indicated by reference $A_{212'-213'}$, the reference used hereafter as the length of the projection. The vertical distance from position 205' to bone 18 (at a position 211'), is indicated by a reference $A_{205'-211'}$. A distance $A_{205'-212'}$ is half the vertical distance between positions 205' and 209'. $A_{205'-212'}$ and $A_{205'-211'}$ may be determined by:

$$A_{205'-211'} = h - \frac{A_{212'-213'}}{2}\sin\varphi \quad (8)$$

$$A_{205'-212'} = \frac{A_{212'-213'}}{2}\sin\varphi$$

The distance between transmitter position 205' and first position 206' (i.e., $A_{205'-206'}$) may be determined by:

$$A_{205'-206'} = \frac{h - \frac{A_{212'-213'}}{2}\sin\varphi}{\cos\gamma} \quad (9)$$

Accordingly, $T_{205'-206'}$ may be determined by:

$$T_{205'-206'} = \frac{h - \frac{A_{212'-213'}}{2}\sin\varphi}{V_S \cdot \cos\gamma}. \quad (10)$$

$T_{207'-209'}$ can be determined using the following formula:

$$T_{207'-209'} = \frac{h + \frac{A_{212'-213'}}{2}\sin\varphi}{V_S \cdot \cos\gamma} \quad (11)$$

and $T_{206'-207'}$ by:

$$T_{206'-207'} = \frac{A_{212'-213'}}{V_B}\cos\varphi - \frac{2h\tan(\gamma)}{V_B}. \quad (12)$$

Therefore, $T_{total}$ can be calculated according by:

$$T_{total} = \frac{2h\cos\gamma}{V_S} + \frac{A_{212'-213'}}{V_B}\cos\varphi. \quad (13)$$

In a preferred embodiment of the invention, a plurality of measurements of $T_{total}$ are performed under different conditions, so as to generate a set of equations in which $V_S$, $V_B$, φ and h are dependent on the plurality of measurements of $T_{total}$ ($\gamma$ is a direct function of $V_S$ and $V_B$, so it is not treated as a separate variable). In some preferred embodiments of the invention, one or more of the above dependent variables may be estimated, thereby simplifying the equations and requiring fewer measurements of $T_{total}$.

Figure 2:
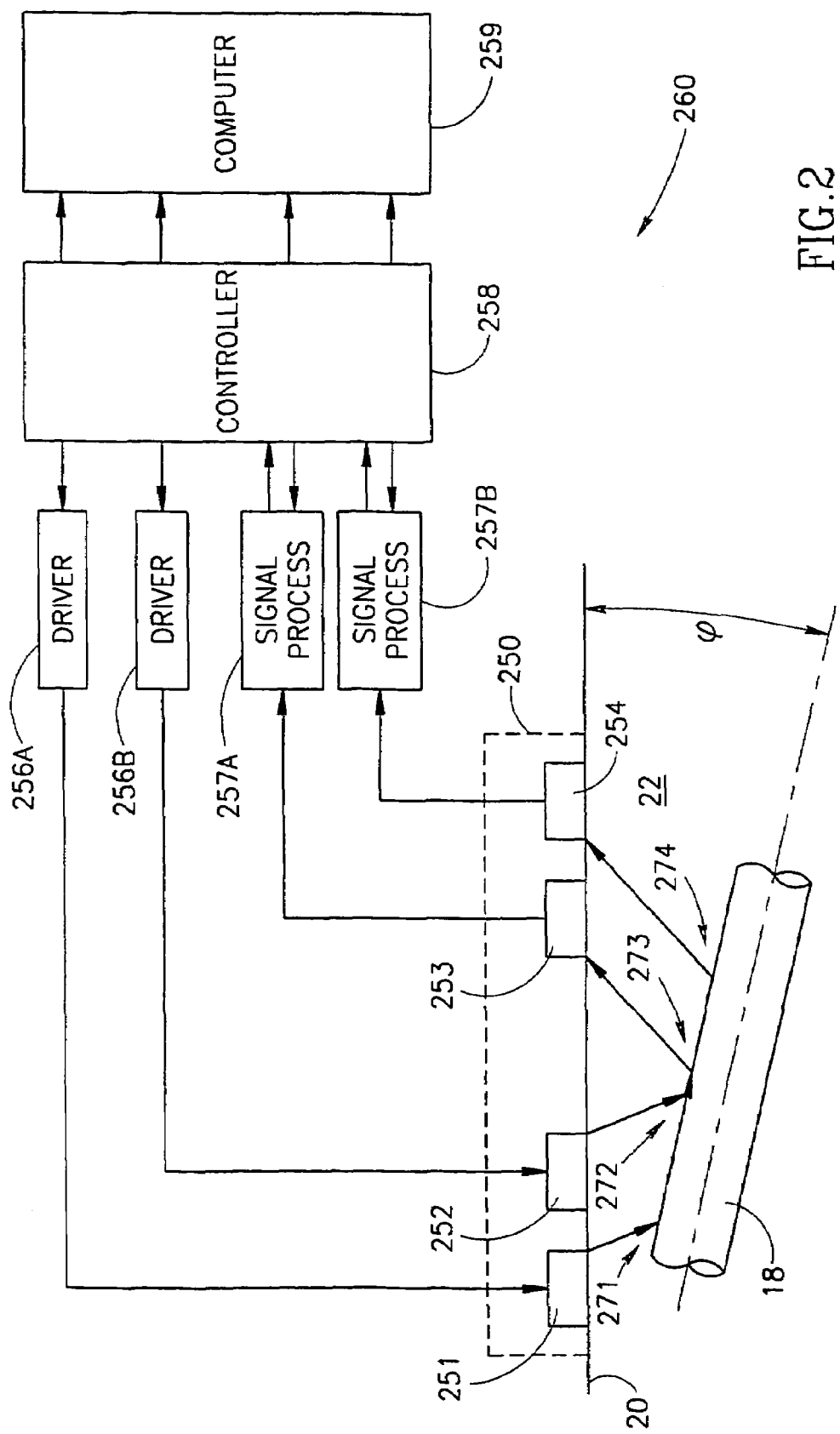
FIG. 2 illustrates apparatus for acoustic bone velocity determination, in accordance with a preferred embodiment of the invention.

FIG. 2 illustrates an ultrasonic measurement system 260 suitable for such multiple measurements, in accordance with a preferred embodiment of the invention. System 260 includes a probe 250 including four ultrasonic elements, preferably two transmitters 251 and 252 and two receivers 253 and 254. Preferably, the ultrasonic elements comprise piezoelectric ceramic transducers. As can be appreciated, four different transducer pairs may be defined in this probe, each of which provides one independent measurement of $T_{total}$ for the above mentioned set of simultaneous equations. In other configurations, the number of transmitters and/or receivers may be different. Additionally or alternatively, at least one of the ultrasonic elements may be used both as a transmitter and as a receiver. In one exemplary embodiment, one transmitter is matched with three receivers, thereby defining only three wave paths. The requirement for a fourth path for solving the four equations in four unknowns is eliminated by estimating a value for one of the unknown variables. Alternatively, a single receiver may be matched with three transmitters. Additionally or alternatively, extra paths (a number greater than the number of variables/equations) may be defined, to provide a more robust estimate of the acoustic bone velocity.

System 260 preferably includes a first high-voltage short-impulse driver 256A coupled to first transmitter 251, and a second high-voltage short-impulse driver 256B coupled to second transmitter 252. The voltage drivers preferably translate a signal from a controller 258 into a high voltage signal having a peak to peak voltage of 300V. System 260 preferably includes first and second signal processors 257A, 257B. In addition, some signal processing may be performed by controller 258. Each of signal processors 257A, 257B preferably includes an amplifier and a transforming device. Signal processor 257A is coupled to receiver 253, and signal processor 257B is coupled to receiver 254. Controller 258 is coupled to first and second high-voltage short-impulse drivers 256A, 256B, and to first and second signal processors 257A, 257B. Controller 258 preferably regulates the transmission, reception and/or preliminary processing of acoustic waves. A computer 259 is preferably coupled to controller 258 for further processing of information received from controller 258 and/or for controlling controller 258. Computer 259 preferably stores measurement results and/or patient information and/or other information in local memory, preferably a database. Additionally or alternatively, computer 259 may transmit and/or receive such information from a remote location, utilizing wired, wireless and/or computer readable media. In a preferred embodiment of the invention, stored results are used to compare a particular measurement to other measurements of the same patient, at different times and/or at different body locations and/or probe orientations. Additionally or alternatively, the stored results may be used as a base line for various populations.

In a preferred embodiment of the invention, system 260 is used in the following manner. As a preliminary step for a bone velocity determination process, an acoustic grease, preferably a water based acoustic coupling gel, silicone gel and/or mineral oil, is applied to the surface of skin 20. Probe 250 is then positioned on the acoustic grease. The measurement process is preferably preceded by a test measurement from which it may be determined that a bone is actually in the field of view of the probe and/or that a proper probe size has been selected.

A plurality of measurements of wave propagation time are initiated by generating ultrasonic waves at one or both of transmitters 251 and 252. If the two transmitters are simultaneously excited, they preferably utilize different wavelengths, so that it is possible to determine, at receivers 253 and 254, which transmitter initiated an ultrasonic wave. In a preferred embodiment of the invention, the transmitted waves have a very fast rise time, for example 20 nanoseconds. Additionally or alternatively, the waves have a moderate duration, for example 0.5 μs. In a preferred embodiment of the invention, the rise time is made as short as possible, to increase the temporal accuracy of detecting a first ultrasonic wave received from a bone. The duration of the wave is preferably short enough so that the probe and measured tissue relax between consecutive measurements and/or so that any acoustic waves created by the transmitters die out.

In a preferred embodiment of the invention, transmitters 251 and 252 transmit a broadband pulse, preferably centered around 1.25 MHz. It should be noted that since the distance that the waves travel in the bone are short, frequencies higher than those used in the prior art are practical, in spite of the higher attenuation of high frequency sound waves in bone. In general, higher frequencies give more precise results than do lower frequencies. Thus, higher frequencies may be used in some preferred embodiments of the invention, for example, 2, 5, 10 or even 20 MHz. Typically the first wave detected by the receivers is a narrow band wave including mainly the frequency component which travels fastest in a particular configuration. Thus, a single broadband transmitted wave may be used. This wave comprises a plurality of frequencies, with the most appropriate frequency being automatically selected by the filtering properties of the soft-tissue and bone. As described below, the identification of the fastest frequency may be used to determine certain other characteristics of the bone, for example, a thickness of its cortex.

In a preferred embodiment of the invention, four travel times are measured, namely: $T_{251\text{-}253}$, $T_{251\text{-}254}$, $T_{252\text{-}253}$ and $T_{252\text{-}254}$. The nomenclature $A_{x\text{-}y}$ is used to indicate the distance between point x and point y. When x and y are ultrasonic elements, the distance is the distance between the elements. In a preferred embodiment of the invention, the travel times are measured by detecting a first ultrasonic wave which arrives at an ultrasonic receiver after one or both transmitters are energized.

In a preferred embodiment of the invention, a noise amplitude threshold is defined which a detected wave must pass. Preferably the noise threshold is a characteristic of a particular probe and/or of a particular receiver, transmitter and/or a receiver/transmitter pair. Additionally or alternatively, the noise threshold may be determined by measuring noise levels prior to energizing the transmitters. Preferably, a time window is defined for each measurement. Alternative methods of determining travel time are described below. Additionally or alternatively, other travel time determination methods known in the art may be used. The following equations may be set-up, based on the methodology discussed above, with respect to FIG. 1 and utilizing various known values and unknowns of system 260 and utilizing measured travel times:

For a first travel time, $T_{251-253}$:

$$V_B \cdot T_{251-253} - \frac{2K_1}{\tan(\gamma)} = A_{251-253} \cdot \cos\varphi \quad (14a)$$

$$K_1 = h - \frac{A_{251-254} - A_{251-253}}{2} \cdot \sin\varphi$$

For a second travel time, $T_{252-254}$:

$$V_B \cdot T_{252-254} - \frac{2K_2}{\tan(\gamma)} = A_{252-254} \cdot \cos\varphi \quad (14b)$$

$$K_2 = h + \frac{A_{251-254} - A_{252-254}}{2} \cdot \sin\varphi$$

For a third travel time, $T_{251-254}$:

$$V_B \cdot T_{251-254} - \frac{2h}{\tan(\gamma)} = A_{251-254} \cdot \cos\varphi. \quad (15)$$

For a forth travel time, $T_{252-253}$:

$$V_B \cdot T_{252-253} - \frac{2h}{\tan(\gamma)} = (A_{251-253} + A_{252-254} - A_{251-254}) \cdot \cos\varphi \quad (16)$$

Thus, four equations utilizing the four unknowns ($V_B$, $V_S$, h, and $\phi$) are generated. If one of the unknowns is estimated, for example by estimating a soft tissue velocity to be 1540 m/s, only three equations are needed to solve for the three unknowns.

In a preferred embodiment of the invention, the equations are solved for each of the unknowns. As can be appreciated, some solving methods may be performed in an off-line manner, so that a suitable software may be generated where the measured values are simply plugged into the software to discover the values of one or more unknowns. Alternatively or additionally, some solution methods may suggest a particular algorithmic construct. Additionally or alternatively, other methods of solution known in the art may be used, for example, iterative methods.

Solving equation (16) for h:

$$h = \frac{V_B \cdot T_{251-254} \cdot \tan(\gamma)}{2} - \frac{A_{251-254} \cdot \tan(\gamma)}{2} \cdot \cos\varphi \quad (17)$$

Solving for (p, using equations (15), and (16):

$$\cos\varphi = \frac{V_B \cdot (T_{251-254} - T_{252-253})}{2A_{251-254} - A_{251-253} - A_{252-254}} \quad (18)$$

applying equations (17) and (18) to equations (14a) and (14b), yields:

$$\begin{cases} V_B \cdot (T_{251-253} - T_{251-254}) + (A_{251-254} - A_{251-253}) \cdot \\ \quad \frac{V_B(T_{252-253} - T_{251-254})}{2A_{251-254} - A_{251-253} - A_{252-254}} + \\ \frac{A_{251-254} - A_{251-253}}{\tan\gamma} \sqrt{1 - \frac{V_B^2(T_{252-253} - T_{251-254})^2}{(2 \cdot A_{251-254} - A_{251-253} - A_{252-254})^2}} = 0 \quad (19) \\ V_B \cdot (T_{252-254} - T_{251-254}) + (A_{251-254} - A_{252-254}) \cdot \\ \quad \frac{V_B(T_{252-253} - T_{251-254})}{2 \cdot A_{251-254} - A_{251-253} - A_{252-254}} - \\ \frac{A_{251-254} - A_{252-254}}{\tan\gamma} \sqrt{1 - \frac{V_B^2(T_{252-253} - T_{251-254})^2}{(2 \cdot A_{251-254} - A_{251-253} - A_{252-254})^2}} = 0 \quad (20) \end{cases}$$

These equations may be solved, for example by defining $V_S$ as a function of $V_B$, using one equation to define one variable with respect to the other and then applying the result in the other equation yielding a single equation with only $V_B$ as a variable. In one example, $V_S$ is determined as a function of $V_B$ using equation (19):

$$V_S^2 = \frac{(A_{251-254} - A_{251-253})^2}{\frac{(A_{251-254} - A_{251-253})^2}{V_B^2} + M} - \frac{V_B^2}{\frac{(A_{251-254} - A_{251-253})^2}{V_B^2} + M} \cdot \frac{(A_{251-254} - A_{251-253})^2 \cdot (T_{252-253} - T_{251-254})^2}{(2A_{251-254} - A_{251-253} - A_{252-254})^2} \quad (21)$$

$$M = \left[ (T_{251-254} - T_{251-253}) + \frac{(A_{251-254} - A_{251-253})(T_{252-253} - T_{251-254})}{2 \cdot A_{251-254} - A_{251-253} - A_{252-254}} \right]^2 - \frac{(A_{251-254} - A_{251-253})^2 \cdot (T_{252-253} - T_{251-254})^2}{(2 \cdot A_{251-254} - A_{251-253} - A_{252-254})^2} \quad (22)$$

Then $V_B$ can be determined from equation (20). It should be appreciated that the above set of equations is solved for all of the four unknowns. However, it is possible to rewrite the above equations there is only one equation for bone velocity which is dependent directly on the measured travel times. Additionally it should be appreciated that equation 21 may be replaced by an estimate for the soft tissue velocity.

In some preferred embodiments of the invention, one or more of the above four variables may be estimated using a different method than the ultrasonic measurements described herein. In a preferred embodiment of the invention, h is estimated using ultrasonic range measurement of the distance of the bone from the skin. Additionally or alternatively, h may be estimated using X-Ray imaging.

Additionally or alternatively, $\phi$ may be estimated using X-Ray imaging. Additionally or alternatively, $\phi$ may be estimated by performing two measurements of h, one at each side of probe 250. Additionally or alternatively, $\phi$ may be set to zero by rocking probe 250 and performing measurements when $\phi$ is determined to be zero. In a preferred embodiment of the invention, $\phi$ may be determined to be zero if two distance measurements on from points spaced apart on the probe determine a same propagation time to an underlying bone.

Additionally or alternatively, the soft tissue velocity may be calculated using triangulation methods, as described for example in WO 97/13145, the disclosure of which is incorporated herein by reference. In the method of this PCT application, two sides of a triangle of paths through soft tissue are created by reflecting waves from a bone. The third side is formed by the distance between two transducers. Utilizing the three sides or two sides and a known angle (usually 90 degrees), assuming the soft tissue velocity is the same for all three sides and knowing the travel times along two sides it is possible to express the soft tissue velocity as a function of the known travel times and the distance between two transmitters. In a preferred embodiment of the invention, the soft tissue velocity is determined along paths which overlap the paths of waves between transmitters and receivers in accordance with a preferred embodiment of the invention. It should be appreciated that the determined soft tissue velocity is an average of the velocities in fat and muscle. Typically layers closer to the bone comprise more muscle, in which the velocity may be 10% higher than in fat tissue.

In a preferred embodiment of the invention, the above described measurements are repeated several times and averaged, to reduced the effect of noise. Additionally or alternatively, more than the required number of paths are measured. In a preferred embodiment of the invention, this results in a set of over-determined equations, the solution of which is known in the art.

In the above discussion it should be appreciated that each measurement path is independent of the other measurement paths. Thus, there is no requirement that there be an overlap between paths. Further, there is no requirement that the transducers be collinear or even coplanar. It should be appreciated that if the ultrasonic elements do not all lie on a same plane, the effective "h" for a path defined by a pair of ultrasonic elements will not be the same for all pairs. Therefore, as described below, corrections for the effective "h" for each path may be determined. Thus, when the above equations are solved for a particular path, different "h" values are used for each path. Alternatively or additionally, a height correction constant may be used. Alternatively or additionally, the height correction may be determined if enough path travel time measurements are acquired.

Generally however, a large degree of overlap between is desirable, to reduce errors caused by variations in acoustic properties of different body areas. One major source of this variability is that bone is not a homogeneous material. Rather, bone comprises several layers, each with a different hardness (and acoustic velocity). The thickness and composition of layers may vary along the length of a bone. In addition, a bone typically comprises both longitudinal and radial sectors, each with different hardness and acoustic velocity characteristics. In some cases the characteristics change abruptly and in other cases a gradual change exists. In addition, bone usually comprises anisotropy material which presents different acoustic properties in different orientations. The degree and/or direction of the anisotropy qualities may also change as a function of the depth of the bone. Preferably, a system in accordance with a preferred embodiment of the invention is used to scan a significant portion of a bone in different orientations and/or along significant radial and/or axial extents.

To properly compare two bone acoustic velocity results derived from two different measuring sessions, the two measurements must be performed on the same portion of the bone. In particular, the location accuracy along the longitudinal axis of the bone should preferably be on the order of 5 millimeters in long bones, such as the tibia. This accuracy is easy to attain using regular positioning methods, such as marking the location with permanent marker. However, the transverse positioning accuracy should preferably be on the order of hundreds of microns, due to the structure of the bone. Since achieving this accuracy is difficult, the probe is preferably used to scan the bone for at least a certain angular range of transverse orientations. When measuring the bone acoustic velocity, the probe is moved in a transverse direction and a plurality of bone acoustic velocities are determined. The maximum or minimum determined value is used as the reference value for comparison to bone acoustic velocity measurements during other sessions. Additionally or alternatively, the acoustic velocity of bone 18 is measured from several directions on a plane perpendicular to the bone axis, since the cortex of bone 18 typically has a number of different sectors, each of which has a different hardness and acoustic velocity. In a grid embodiment described below, a grid device is preferably utilized to determine a tangential positioning and/or the orientation of a measurement relative to the axis of the bone. Preferably such a grid device is used to simultaneously image the bone.

It should be appreciated that, with some bones, such as the vertebrae, measuring softer sectors may be more practical than measuring harder sectors, hence the search for the minimum velocity. The minimum determined velocity typically represents travel in the softest sector. A minimum determined velocity found at a later date is also in the softest sector, thus, the velocity measurement is repeated at the same transverse location (same sector).

Additionally or alternatively, the acquired velocity measurements are used to build a transverse and/or axial velocity profile map of bone 18, which is useful for bone structure analysis.

In a preferred embodiment of the invention, probe 250 is oriented to avoid straddling significant body structures, such as large blood vessels. In a preferred embodiment of the invention, large blood vessels are detected by determining Doppler shifts in the spectra of the ultrasonic waves which are reflected by the blood. Additionally or alternatively, such structures are detected visually. Additionally or alternatively, the ultrasonic beams are made significantly wider than such structures, so that their effect is reduced and/or averaged out.

The minimal required distance of wave propagation in the bone using the above described methods may be as short as 5, 3, 2 or even 1 millimeters. Several resolution parameters should be distinguished: the precision of axial and radial placement of the segment of bone being measured; the length of the segment of bone being measured; and the precision in moving the measured area a small amount during a single session. Another important resolution parameter is the accuracy of the velocity measurement itself. It should be appreciated that using a grid type probe, as described below allows one or more of these resolutions to be enhanced.

The preferred distance between the transmitters and the receivers depends on the soft tissue thickness. Using methods described herein, high resolution mapping of relatively uneven bones is possible. For example, such bones include the vertebra, the small bones in the wrist and portions of bone near joints. In addition, it is possible to measure the bone velocity in both longitudinal and transverse directions, since the length of the measured bone segment can be very short, even relative to a radius of a bone. In a preferred embodiment of the invention, the probe is made curved. Preferably, the radius of the curve is selected to conform to an expected radius of an underlying bone.

The small dimensions of the minimally required bone path segment make it possible to scan with a high spatial resolution, using embodiments of the present invention. For example, to measure the acoustic velocity in a portion of the cortex of a tooth, a 10 MHz ultrasonic pulse can be used. Due to the high frequency of the ultrasound, the probe dimensions can be in the order of 3 millimeters and the resolution better than 1 millimeters.

A single measurement of a bone velocity in some preferred embodiments of the invention is made over a time period only 1.5 milliseconds long, which is faster than most body rhythms. Several measurements taken along the course of a body rhythm can be used to measure the effect of the body rhythm on the measurement. In some cases the body rhythm adds an uncertainty in determining paths and/or changes in soft tissue velocity. Alternatively or additionally, it is the effect of a body rhythm on $V_S$, $V_B$, $\phi$ or h which it is desirable to measure. In a preferred embodiment of the invention, 40 single measurements are performed and averaged over a time period of about 100 ms. The average value is presented as an estimated bone velocity. In a preferred embodiment of the invention, the measurements are analyzed to determine their distribution and/or checked for internal consistency. An average mapping session typically includes measuring acoustic velocity at about 100–200 points around the circumference of the bone.

Alternatively to using a broadband transmitted wave, a single frequency pulsed wave may be used, since in some preferred embodiments of the invention the only aspect of the wave analyzed is the time of first reception of a wave. Alternatively, other, more complex wave forms or pulses are used and the received waves are analyzed. It should be appreciated that the transmitting and receiving steps of the above described process can be performed in either order and can also be performed simultaneously. Preferably, different frequencies are used for each wave. Alternatively or additionally, the pulses are timed, so that no two pulses arrive together at a single receiver.

A four element probe, such as described above with reference to FIG. 2, is preferably constructed to be less than 100 millimeters long, more preferably less than 50 millimeters long and in some preferred embodiments less than 3 millimeters long. In a specific preferred embodiment of the invention, the probe is 32 millimeters long. Due to the very high accuracy requirements from such a probe, the probe body and/or structural elements and/or filler materials and/or spacing elements are preferably constructed from a material which does not substantially expand or shrink in the temperature range of 15–40° C. Such materials typically comprise a mixture of a material which expands when heated from 15 to 40° C. and a material which shrinks when heated from 15 to 40° C.

In a preferred embodiment of the invention, the distance between the ultrasonic elements is optimized for a certain expected soft tissue depth. Thus, a typical operational system comprises several probes, each suitable for a different range of depths. As described below, a probe connector may include a electrical indication of its type. Alternatively, a single grid-type probe, as described hereinbelow, is used.

Typically, the probe is not constructed to an absolute precision of distance between each ultrasonic element. Instead, a probe is constructed with a precision of approximately 0.1 millimeter, and the exact distances between the elements are measured using a phantom. The results of the measurement, having a typical precision of better than 2 μm, are stored in computer 259 for use in the velocity determination as described in greater detail below. Such a phantom preferably comprises a plastic cylinder which has a cylindrical metal core with steps formed along its axis embedded within the plastic. Each step corresponds to a different known depth of the plastic overlying the metal core. When a phantom is measured with the probe, the acoustic velocity determination equations are preferably inverted so that the distance between the ultrasonic elements of the probe is now a function of known depths and acoustic velocities and measured travel times. Alternatively or additionally to using such a phantom, a hard plate having a known ultrasonic velocity may be used to directly measure propagation time between transmitters and receivers. In a preferred embodiment of the invention, the temperature dependence of acoustic velocity in the material is also known. The thickness of the plate is preferably at least 20 mm to be longer than the wavelength and to delay reflections from plate-air boundaries.

In a preferred embodiment of the invention, two plates having different known ultrasonic velocities are utilized for calibration. In each plate, at least three wave travel times are measured, between pairs of transmitters and receivers. In a preferred embodiment of the invention, the travel time between the inner pair of transmitter and receiver is not measured. Also during ultrasonic bone velocity measurement, this inner pair is preferably not measured. Two plates and three measurements in each plate yield six independent equations. Six variables may be calibrated from these equations. The variables are preferably the three distances between the ultrasonic elements and three average heights of ultrasonic elements from the measurement plate, i.e., the effective thickness of an acoustic chamber separating the ultrasonic elements from the plate, (described below). Each average height represents an average height which may be used in an equation which represents traveling of waves between that particular transmitter/receiver pair. Alternatively to three measurements in two plates, other numbers of measurements may be performed in other numbers of plates to yield a set of desired equations for calibration.

In a preferred embodiment of the invention, a probe may be mechanically configurable to match a particular measurement situation. Such configuration may include changing the distance between ultrasonic elements and/or their pitch angle. Preferably, after the ultrasonic elements are properly positioned and fixed in place, their exact locations are preferably determined by measuring the travel time in a plate as described above.

Figure 3:
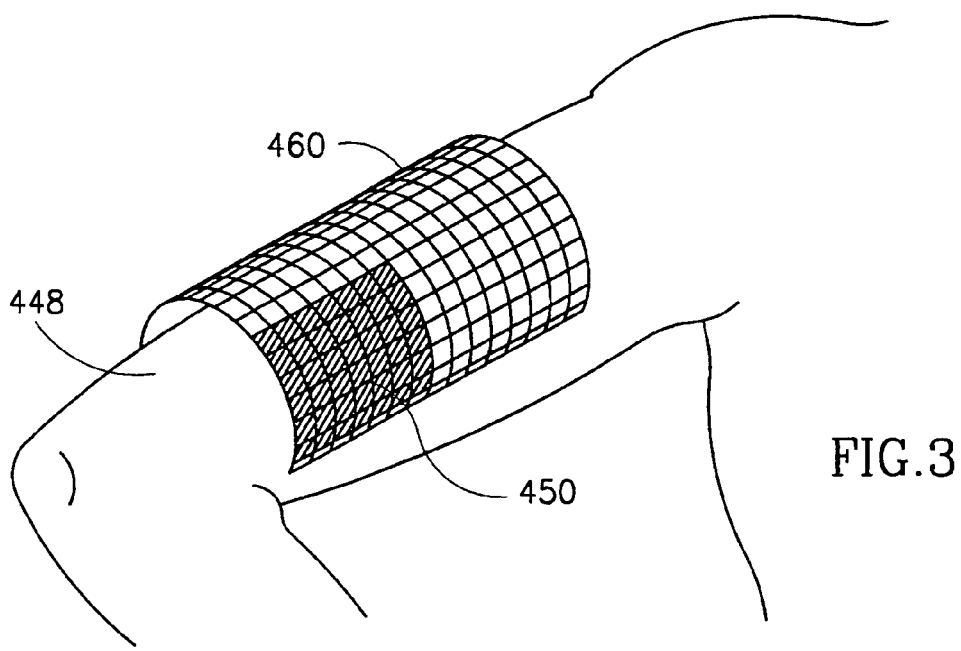
FIG. 3 is a schematic illustration of an alternative embodiment of the present invention utilizing an array of piezoelectric transducers.
Figure 4:
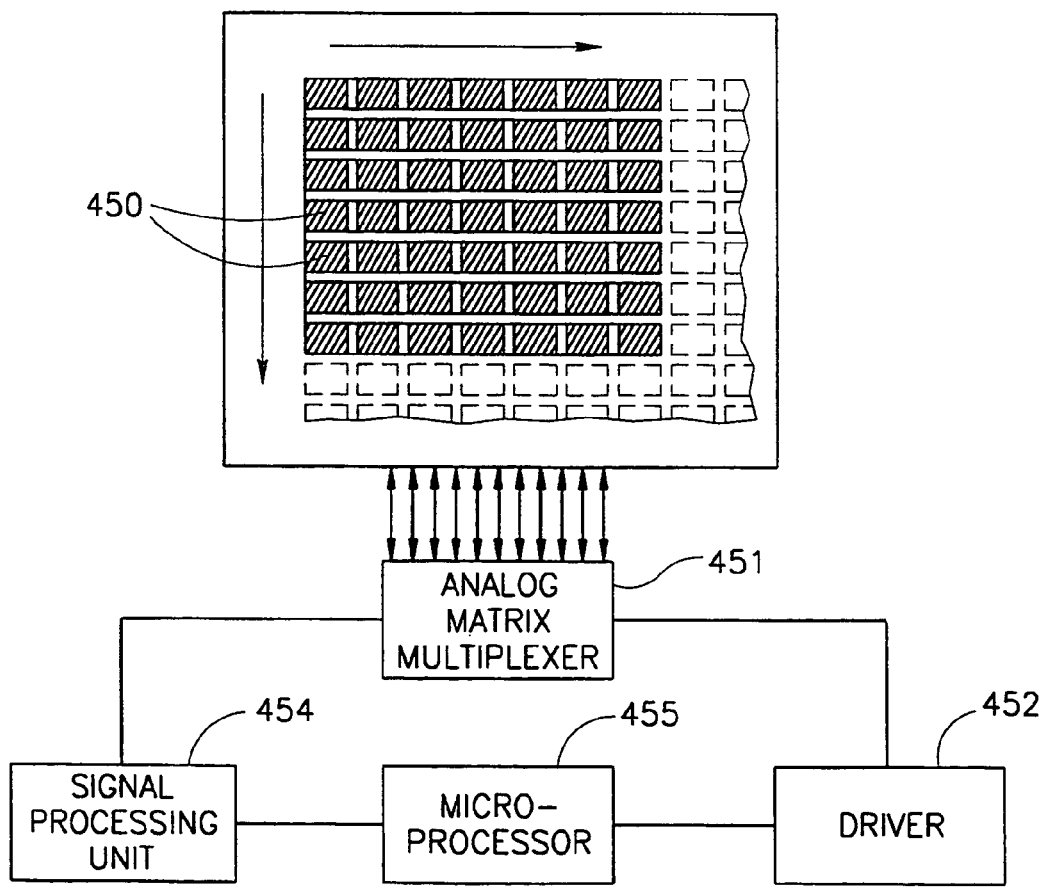
FIG. 4 is a schematic illustration of the array of FIG. 3, illustrating the connections of the transducers to control and signal processing elements.
Figure 5:
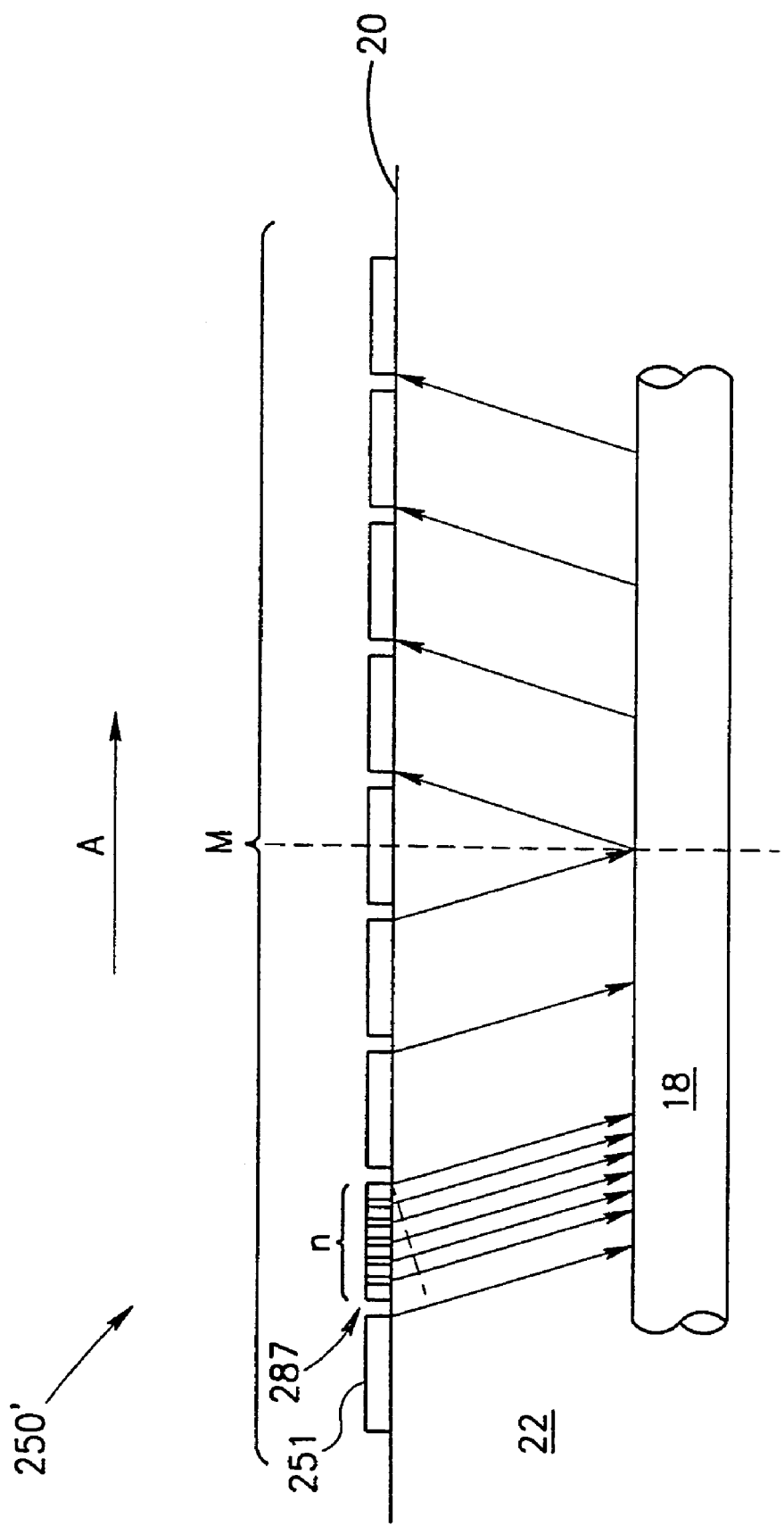
FIG. 5 illustrates using a phased array acoustic probe, in accordance with a preferred embodiment of the invention.

Reference is now made to FIG. 3, FIG. 4 and FIG. 5 which illustrate aspects of a further embodiment useful for scanning across a section 448 of a human body, such as an arm.

In this embodiment, a probe device formed of an array of ultrasonic transmitter/receiver cells 450 is placed onto or wrapped around section 448 or is formed into a sock-like element 460. The cells of array 450 are preferably formed from a piezoelectric material, such as a piezoelectric plastic or ceramic. Array 450 is typically acoustically coupled to section 448 in a standard manner, for example, using acoustic coupling grease.

Typically, as shown in FIG. 4, the input and output leads of each cell of array 450 are connected to an analog matrix multiplexer 451 which, in turn, is connected to a driver 452 and to a signal processing unit 454. Driver 452 and unit 454 are typically controlled via a microprocessor 455.

Multiplexer 451 enables each cell of array 450 to be individually accessed and is operative to define each cell as a receiver, a transmitter, a transmitter/receiver or as non-active.

The cells of array 450 may individually be too small to form ultrasonic transducers for use in prior art methods, due to the attenuation caused by long paths through bone 18. Therefore, a plurality of groups of cells of array 450 in desired locations were electronically and selectably defined to be the ultrasonic elements. In a preferred embodiment of the present invention, each cell of array 450 is a separate ultrasonic element as described herein. Alternatively, groups of cells are defined as transducers, as shown in the prior art. However, when groups are so defined, one of the preferred operation modes described below is preferably used.

A first preferred method of operation is to select cells and groups of cells that approximate the functionality of the embodiments described hereinabove. Thus, optimal placement of transmitter/receivers can be achieved without moving ultrasonic elements and/or the probe.

In a preferred embodiment of the invention, a two step method is used to determine the configuration of array 450 as transmitters and receivers. As described hereinabove, a preferred embodiment of the invention uses probes which are optimized for a specific soft tissue thickness between the probe and bone 18. Using array 450 to image bone 18 it is possible to determine the thickness of underlying soft tissue 22, before bone velocity determination. A, a method of optimally configuring an array of elements, according to a preferred embodiment of the invention, comprises:

(a) determining the thickness of underlying soft tissue 22; and (b) configuring array 450 into transmitters, receivers and transmitter/receivers having optimal distances therebetween, which are calculated based on the determined thickness of soft tissue 22.

The thickness may be estimated using a time-of-flight method which assumes a soft tissue velocity of 1540 m/s. Alternatively or additionally, several pre-measurements are performed to determine a desirable bone path length and/or other parameters of the measurement.

A preferred method of operation maps bones and soft tissues by operating different cells of array 450 instead of physically moving a unit comprising a plurality of ultrasonic units. Thus, the bone velocity at different positions and in different directions can be measured without physically moving the apparatus.

FIG. 5 shows a multi-element probe 250', including at least one subdivided element 287, which is subdivided into "n" sub-elements. Probe 250' preferably comprises "M" elements, each of which may be subdivided. In a preferred embodiment of the invention, the "n" sub-elements are actuated with a predetermined phase shift of a wave, to generate a beam having desired characteristics, such as direction and focusing. Using the above-described grid elements, it is possible to relocate a measuring zone on surface of the bone in a direction A, without moving probe 250'.

In a preferred embodiment of the invention, a single grid type imaging probe is used for imaging, for soft tissue velocity determination and/or for bone velocity mapping. In some cases, different measurement schemes may be used for each type of measurement. Alternatively or additionally, two different methods of measurement may be to measure a single property, such as bone velocity or soft tissue velocity.

Preferably, the transmitters and/or receivers are oriented to preferentially emit and/or receive their waves at an angle which is the estimated critical angle. In a preferred embodiment of the invention, the ultrasonic waves are transmitted as pencil beams. Alternatively or additionally, the waves are focused at the estimated or measured distance to the bone, preferably along a (desired) path which the waves are expected to follow.

It is known that the velocity of ultrasound in a purely cortical bone is approximately 3000 m/s–4700 m/s (which corresponds to a Critical angle of approximately 19–°–31°), and the velocity in trabecular bones with a thin surface layer of cortical bone is approximately 1650 ml/s–3000 m/s (which corresponds to the critical angle of approximately 31°–69°).

Figure 6:
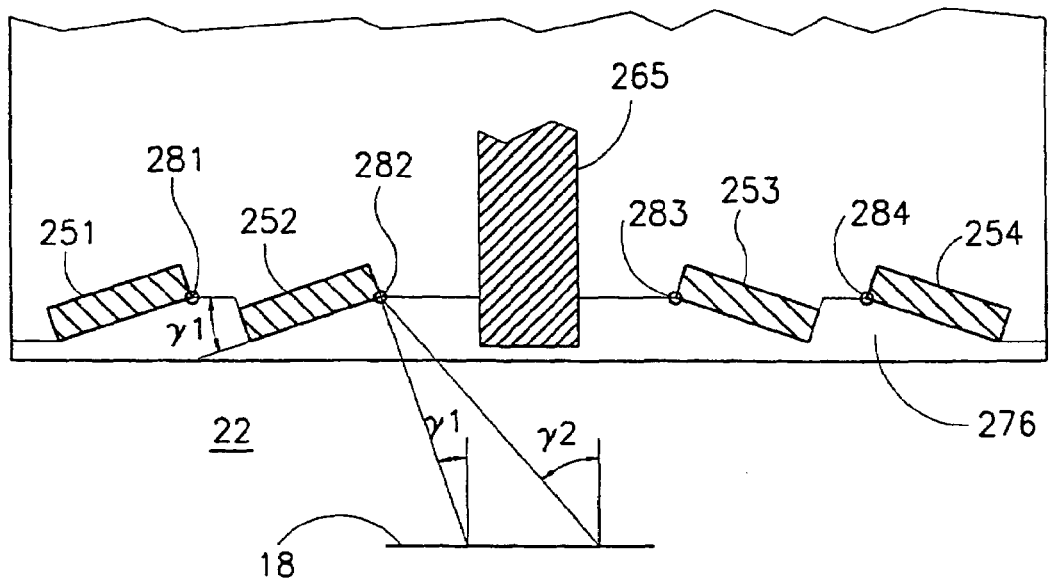
FIG. 6 and FIG. 7 illustrate an effect of ultrasonic element pitch on an operating characteristic of a probe in accordance with a preferred embodiment of the invention.
Figure 7:
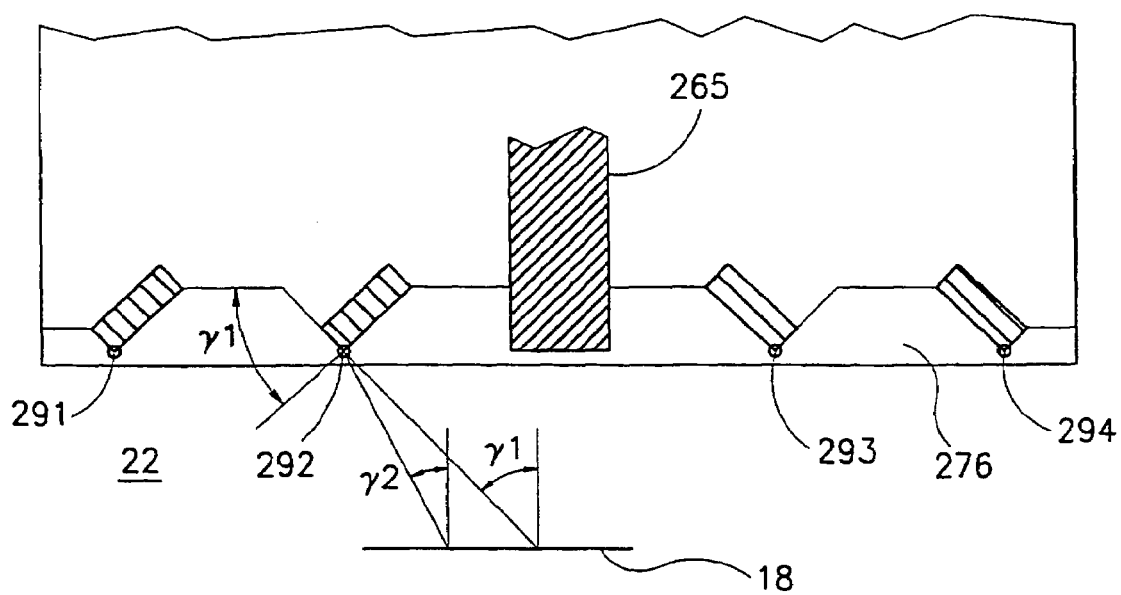

FIG. 6 and FIG. 7 illustrate an effect of ultrasonic element pitch on an operating characteristic of a probe in accordance with a preferred embodiment of the invention. A width of the first and second transmitters 251, 252, and a width of the first and second receivers 253, 254 are preferably selected based on desired wavelength characteristics of the ultrasonic elements and an angle of a pitch of the transmitters 251, 252 and/or receivers 253, 254 is determined with respect to the horizontal plane. As a result of the pitch of the transmitters 251, 252 and/or receivers 253, 254, a region 276 is defined below the pitched transmitters 251, 252 and/or the pitched receivers 253, 254. Region 276 is also called an acoustic chamber. Region 276 may be filled by a liquid, by an elastic material, for example, silicone rubbers, for example, RTV630, manufactured by General Electric Inc., US or polyurethane rubbers, for example EL-110H, manufactured by Robner, UK or by a relatively hard material, for example, hard polyurethane such as U146A and a chain extender UL143 manufactured by Polymer Gvulot. The acoustic parameters of region 276, including one or more of a speed of sound, acoustic impedance and acoustic absorption, are preferably selected to optimize different characteristics of probe 250.

In a preferred embodiment of the invention, probe 250 includes at least one barrier element 265 (shown in FIGS. 6 and 7) which is preferably an acoustic attenuator. In a preferred embodiment of the invention, the barrier element is used to delay and/or attenuate ultrasonic waves which travel through the probe itself. Generally, paths along which the wave travels faster than along the bone inclusive paths are termed "parasitic paths".

As shown in FIGS. 6 and 7, the actual angle between the ultrasonic elements and the bone is dependent on the edge of the transmitter from which the wave is generated. The angle may be a physical angle or an angle generated using a phased array. Typically, a pencil beam is used so that a particular inclination angle defines a range of angles $\gamma_1$ and $\gamma_2$ between which measurement conditions are optimal. As described above, the required range of angles depends on the soft tissue velocity, angle relative to the parallel of the bone and bone velocity. These parameters may be controlled to some extend by a user, however, many parameters depend on physiological characteristics which are determined by the age or sex of the patient and/or the particular body portion which is the subject of the measurement. In a preferred embodiment of the invention, the distances between the ultrasonic elements as used in the above equations are determined by the inclination angle of the elements. In general, when a low inclination angle is used, the upper (internal) end of the ultrasonic element is effective and when the inclination angle is high, the lower (external) end of the ultrasonic element is effective. Generally, the inclination angle is selected to higher when a lower bone velocity is to be measured. For example, in FIG. 6 the upper end of an element and in FIG. 7 the lower end of an element. In a preferred embodiment of the invention, the determination of which end is used may be based on an estimate of the above described variables. Alternatively or additionally, an iterative evaluation method may be preferred, in which the results of one stage are used to estimate the values for constants in a next stage. In a preferred embodiment of the invention where a grid type probe is used, the piezoelectric element itself is flat, so there is no problem of upper or lower ends, even when the beam is inclined.

As indicated above, one aspect of some preferred embodiments of the invention is to reduce parasitic waves. In a preferred embodiment of the invention, parasitic waves are reduced by placing a plurality of acoustic barriers in probe 250. Thus, any parasitic wave is required to travels a torturous path between transmitter and receiver elements. In a preferred embodiment of the invention, the barriers are placed to create a labyrinth. In addition to parasitic waves which travel in the probe body, some parasitic waves can travel through the acoustic chamber. In a preferred embodiment of the invention, barrier 265 extends through the acoustic chamber to the skin. In some preferred embodiments of the invention, barrier 265 protrudes from probe 250, to cause an indentation in the soft tissue when probe 250 is pressed against the skin.

In a preferred embodiment of the invention, probe 250 and/or the acoustic chamber are formed of an acoustically attenuating material. Thus, parasitic waves cannot travel through the probe with any significant intensity. By making the acoustic chamber attenuating, any ultrasonic wave which does not immediately exit the chamber is extremely attenuated by travel through it. One example of a parasitic wave which is thus attenuated is a wave which travels through the acoustic chamber and enters the soft tissue to "bypass" barrier 265. In a preferred embodiment of the invention, the acoustic chamber comprises acoustical windows so that ultrasonic waves which travel along desirable paths (at about the expected critical angle) are less attenuated than other waves. Such windows may be formed by varying the composition of the material of the acoustic chamber and/or by various methods of post treatment of the material.

Alternatively or additionally, probe 250 and/or the acoustic chamber are filled with a material having a low acoustic velocity, so that parasitic ultrasonic waves are slowed down.

In a preferred embodiment of the invention, the acoustic chamber is filled with U-146 Polyurethane (1920 m/s, 5.5 dB/cm), which undergoes finely bubbled phase separation when it polymerizes. Alternatively or additionally, polyutherane EL-110H (1620 m/s, 3 dB/cm), by Robner, UK may be used as a filer material. Alternatively or additionally, PWO-02 (1835 m/s, 15 dB/cm) or PWN-01 (2010 m/s, 20 dB/cm), by CIRS USA may be used. In a preferred embodiment of the invention, higher attenuation materials are used when the distance between a transmitter and a receiver are shorter. Preferably, the path between the inner transmitter and receiver is not measured, so only the next shortest path needs to be taken into account.

Figure 8:
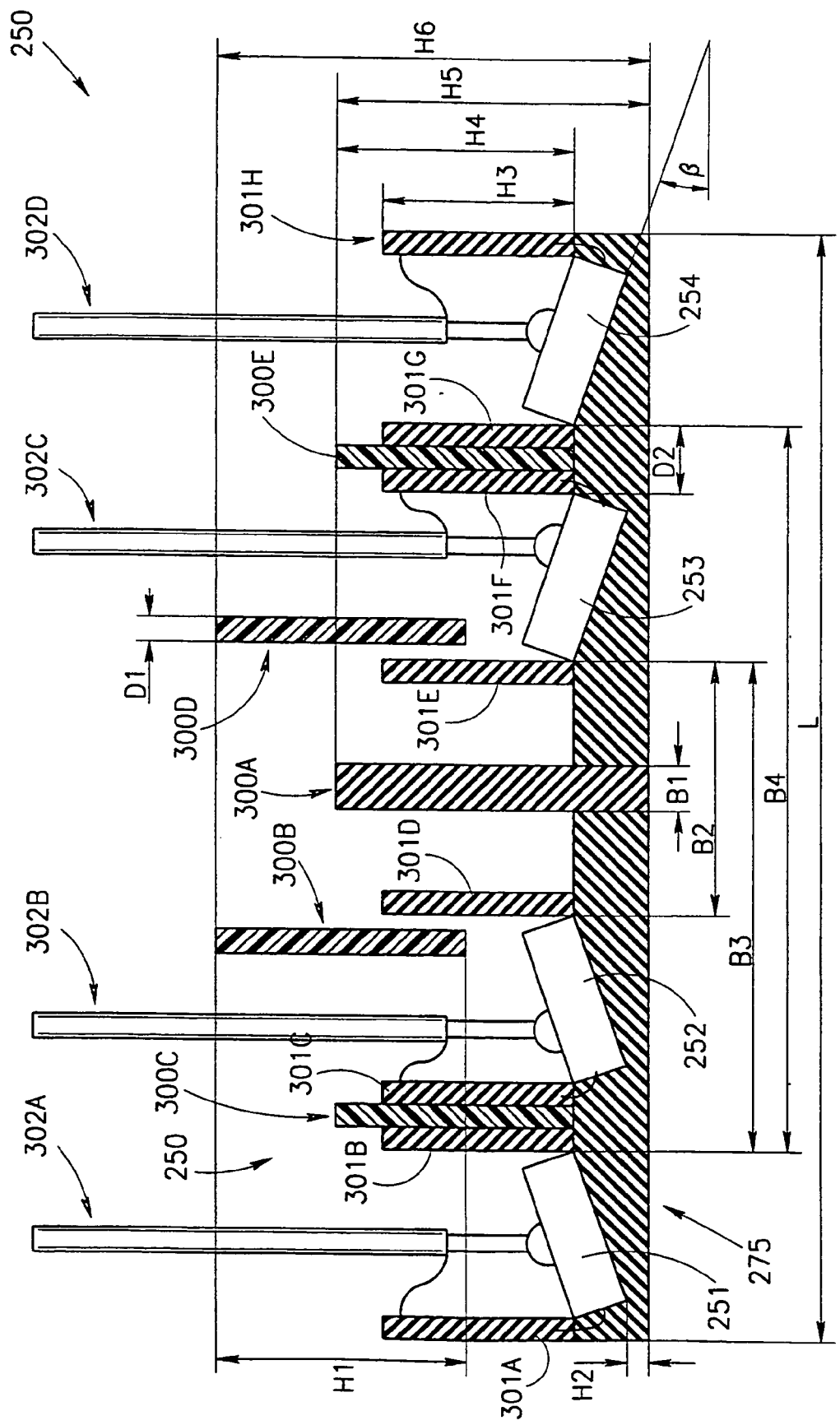
FIG. 8 is a schematic cut-through view of a probe in accordance with a preferred embodiment of the invention.

FIG. 8 illustrates a probe construction in accordance with a preferred embodiment of the invention. Probe 250 preferably includes acoustic barriers, as described above and/or electrical shielding, for isolating the piezoelectric elements from each other. In FIG. 8, each ultrasonic element is electrically shielded by electrical shields on either side thereof, indicated by reference numbers 301A–301H.

Shielded cables 302A–302D are used to connect element drivers and other electronics to the ultrasonic elements. The shielding of the cable is preferably connected to one or both of the electrical shields surrounding each element and then to the bottom face (front surface) of the piezoelectric element. Alternatively or additionally, an acoustic barrier (300A, C, E) is located between each two ultrasonic elements. Alternatively or additionally, acoustic barriers (300B, D) are preferably located between the other acoustic barriers to convert the probe interior into an acoustic labyrinth. In some cases, barriers 300C and 300E may be lowered and/or extended towards the probe surface, especially if the distance between ultrasonic elements is shorter. In a preferred embodiment of the invention, an acoustic barrier is also formed surrounding all the acoustic elements of the probe and separating them from an outside casing of the probe. Preferably, the electrical shielding surrounds each ultrasonic element from all sides. Preferably barriers 300A–300E comprise flat plates which extend between opposite sides of the probe. The blank spaces in FIG. 8 are preferably filled with an attenuating material, as described above.

Figure 9:
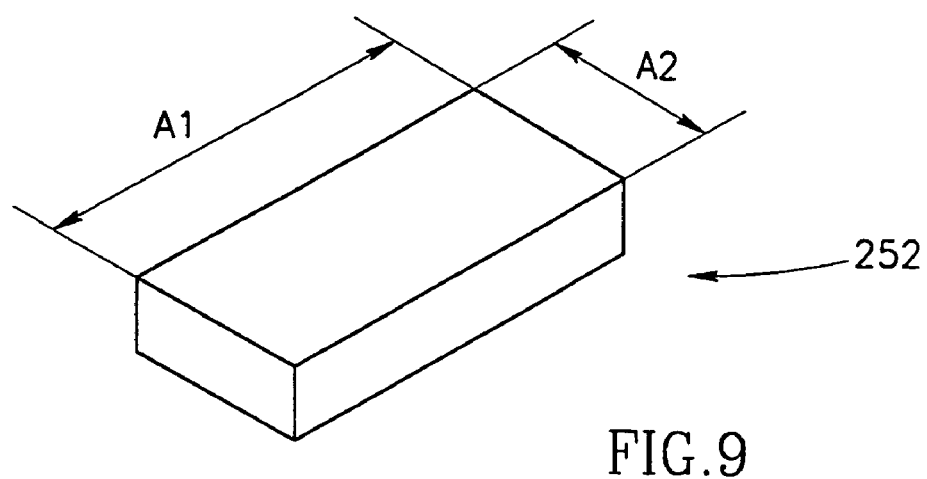
FIG. 9 illustrates an ultrasonic element of the probe of FIG. 8, in accordance with a preferred embodiment of the invention.

FIG. 9 shows an enlarged view of an exemplary piezoelectric element used as a transmitter and/or a receiver, in a preferred embodiment of the invention.

In the embodiment of FIG. 8, the propagation time of a wave generated by transmitters 251 and/or 252, which travels above skin 20 and around the acoustic barriers 300A–300E, is delayed because the elements in the probe 250 are designed in a labyrinth type manner. The dimensions of the acoustic barriers 300A–300E and of the electrical shields 301A–301H are illustrated below in Table 1, for two preferred probe embodiments. As shown in Table 1, the dimensions and characteristics of transmitters 251, 252 and receivers 253, 254, and the distances therebetween, vary depending if the transmitter and/or the receiver are (for a proximal phalanx III analysis or for a radius(hand)/tibia(leg) analysis):

ultrasonic velocity. In a preferred embodiment of the invention, an air-filled probe may be mechanically adjusted periodically, to match specific measurement situations, such as soft tissue depth and expected ultrasonic bone velocity.

Table 2 shows preferred composition materials for the body of probe 250, acoustic chamber 276, acoustic barriers 265, 300A–300E, and electrical shields 301A–301F, and an exemplary list of manufacturers (and the respective part numbers) for these elements:

TABLE 2

| Element | Composition | Manufacture Number | Vendor |
| --- | --- | --- | --- |
| Body of Probe (250) | Polyurethane | U146-0A + chain extender UL 143 | Polymer Gvulot, Israel |
| Acoustic Chamber (276) | Polyurethane | U146-0A + chain extender UL 143 | Polymer Gvulot, Israel |
| Acoustic Barrier (265, 300A-300E) | Neoprene (i.e., expanded rubber) or Polyurethane | CIG-3 2529/14A + isocyanate 44V20 | Regumi 1978 Ltd., Israel Polyurethane Ltd., Haifa, Israel |
| Electrical Shield (301A-301F) | Copper Foil tape | 8271-0050-39 | Instrument Specialties, USA |

Figure 10:
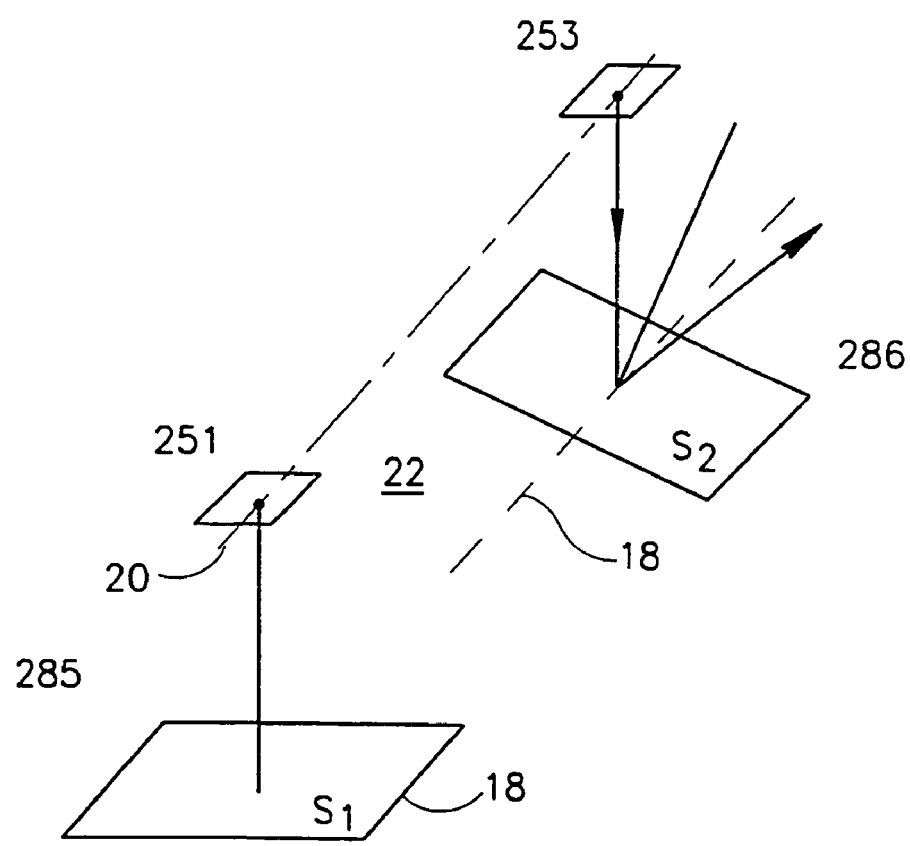
FIG. 10 illustrates a negative interaction between a non-parallel bone presentation and one method of ultrasonic measurement of reflections from a bone.

The devices shown in FIGS. 1–9 (and the method associated therewith) are particularly useful when the plane of the bone 18 is not parallel to the plane of the skin 20. FIG. 10 illustrates a negative interaction between a non-parallel bone presentation and one method of ultrasonic measurement utilizing reflections from a bone. When a reflection is determined from the bone, most of the energy is reflected at the incidence angle. Thus. If the incidence angle is zero (when the presentation is parallel), as shown for element 251, most of the energy is reflected back to element 251. However, if the presentation is non-parallel, as shown for element 253, most of the energy is not reflected back to the ultrasonic element. As a result, there is an increased susceptibility to noise and more difficulty in designing a

TABLE 1

| Probe type | A1 mm | A2 mm | Angle β | F MHz | L mm | B1 mm | B2 mm | B3 mm | B4 mm | D1 mm | D2 mm | H1 mm | H2 mm | H3 mm | H4 mm | H5 mm | H6 mm |
| --- | --- | --- | --- | --- | --- | --- | --- | --- | --- | --- | --- | --- | --- | --- | --- | --- | --- |
| Phalanx | 8 | 2 | 23 | 1.25 | 23.5 | 3 | 11.5 | 15 | 18.5 | 0.5 | 1.3 | 15 | 0.5 | 12 | 17 | 18.5 | 26.5 |
| radius/tibia | 10.5 | 4 | 23 | 1.25 | 40.5 | 4 | 20.3 | 26.1 | 31.9 | 0.5 | 1.75 | 15 | 0.5 | 12 | 17 | 19.5 | 28.5 |

In a further embodiment according to the present invention, a body of probe 250 is separated from a holder (e.g., a probe holder) encasing the probe 250 with further barrier substantially similar composition as that of the barriers 265, 300A–300E. Thus, a wave generated by transmitters 251, 252 cannot travel through the probe holder to receivers 253, 254 and arrive before a wave which travels through a bone and/or its amplitude is reduced. This further barrier preferable has a high acoustic attenuation. As such, a gas-filled (e.g., air filled) gap can serve as the further barrier. In addition, the further barrier can also be composed of sponge materials, porous materials, etc. In a preferred embodiment of the invention, probe 250 is left hollow, since air has a very high attenuation at these high frequencies and/or a low receiver which is sensitive over several orders of magnitude. A possible end result of this problem is a difficulty in determining whether there is a bone surface at a certain distance from the transmitter.

Figure 11:
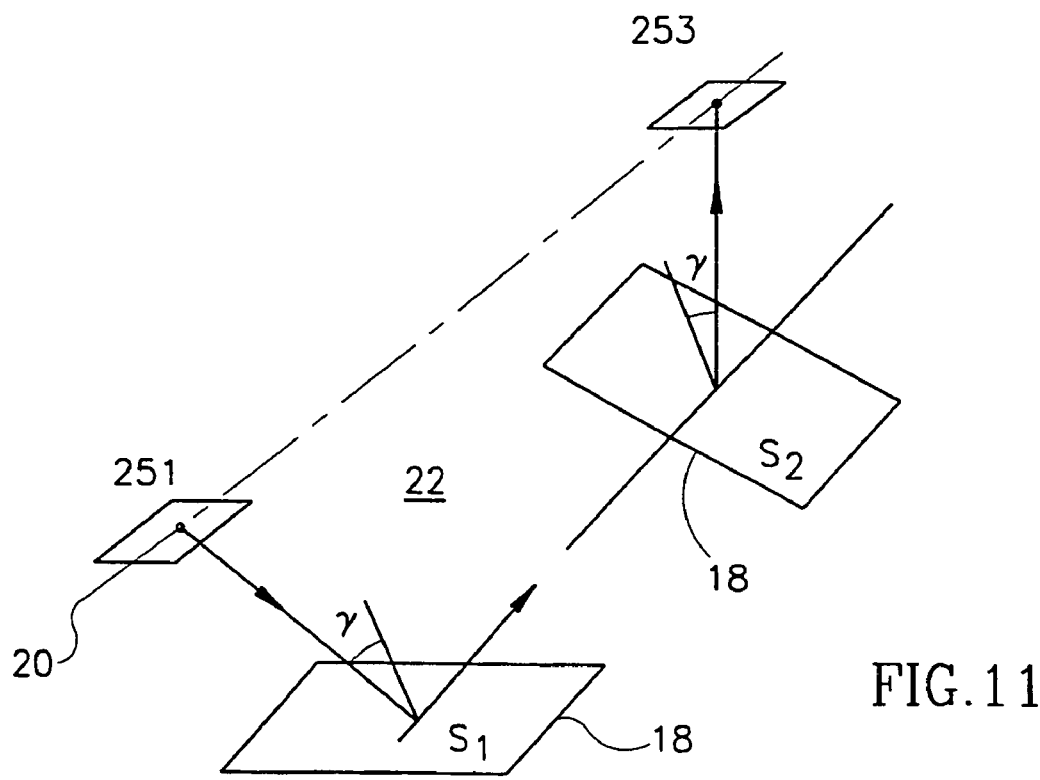
FIG. 11 illustrates an effect of non-parallel bone presentation on a measurement method in accordance with a preferred embodiment of the invention.

FIG. 11 illustrates an effect of non-parallel bone presentation on a measurement method in accordance with a preferred embodiment of the invention. Instead of measuring reflection, some preferred embodiments of the present invention measure only the amplitude of a wave which enters a bone and which is emitted by the bone. The entry of the wave into the bone and the emission of the wave from the bone, as shown in FIG. 11, are much less sensitive to small changes in the angle, as might be expected if the bone surface is uneven. This is especially true if the entry and exit angles and not perpendicular to the bone to begin with.

In a preferred embodiment of the invention, once a probe is calibrated the calibrated parameters are then stored by computer 259 into a Read Only storage device, for example a FLASH ROM. This Read Only storage device is preferably coupled to probe 250 and/or incorporated in the probe 250, so that the calibration of a particular probe 250 is provided on its own Read Only storage device. When probe 250 is coupled to a measuring system using a connection plug, the calibration parameters of probe 250 are preferably retrieved by measuring system via plug terminals and are utilized to measure velocity $V_B$. Alternatively or additionally, at least some signal processing circuitry is incorporated into probe 250 itself, which circuitry may utilize the calibration information. Alternatively or additionally, such Read Only memory may include a probe identification number and/or usage information, which is especially useful when a measurement system is used simultaneously with more than one probe connected thereto.

One or more of the following parameters are preferably calibrated and/or stored on the Read Only memory:

(a) distances between elements;

(b) amplitudes of various parasitic waves;

(c) time limits, minimal and/or maximal, outside of which parasitic waves may arrive at a receiver;

(d) attenuation levels of ultrasonic waves;

(e) transmission and/or reception frequency and/or spatial response of the transmitters and/or receivers;

(f) bandwidth resonance characteristics of the transmitters and/or receivers (g) relative thickness of acoustic chamber underlying individual ultrasonic elements; and (h) chamber material speed of sound, which may include several speeds, one for each operating frequency.

Acoustic bone velocity measurement has many uses. A first use is finding fractures and strains in bones. When a bone is over stressed or fractured (even a hairline fracture which is hard to see in X-ray images), its acoustic velocity chances markedly at the locations surrounding the fracture. Owing to the high resolution of some embodiments of the present invention, fractures in the wrist bones can be identified utilizing preferred embodiments of the invention.

A second use is in estimating the density of the bone and portions thereof to determine the loss of minerals in the bone due to diseases of the bone, osteoporosis or low-gravity environments. It should be noted that the velocity is dependent mainly on Young's Modulus, i.e., the lower the velocity, the weaker the bone.

A third use is to chart the healing process of a broken bone. A common practice today is to keep the damaged bone in a cast until a predetermined period of time has elapsed. However, some patients require a longer or shorter healing period. X-ray images do not usually show enough detail to evaluate the integrity of the bone. By measuring and charting changes in acoustic bone velocity, a physician can more accurately estimate the state of bone repair. In a preferred embodiment, a small hole is drilled in the cast and the acoustic bone velocity is measured without removing the cast. In some patients it is advantageous to compare changes in acoustic bone velocities of opposing limbs.

Figure 12:
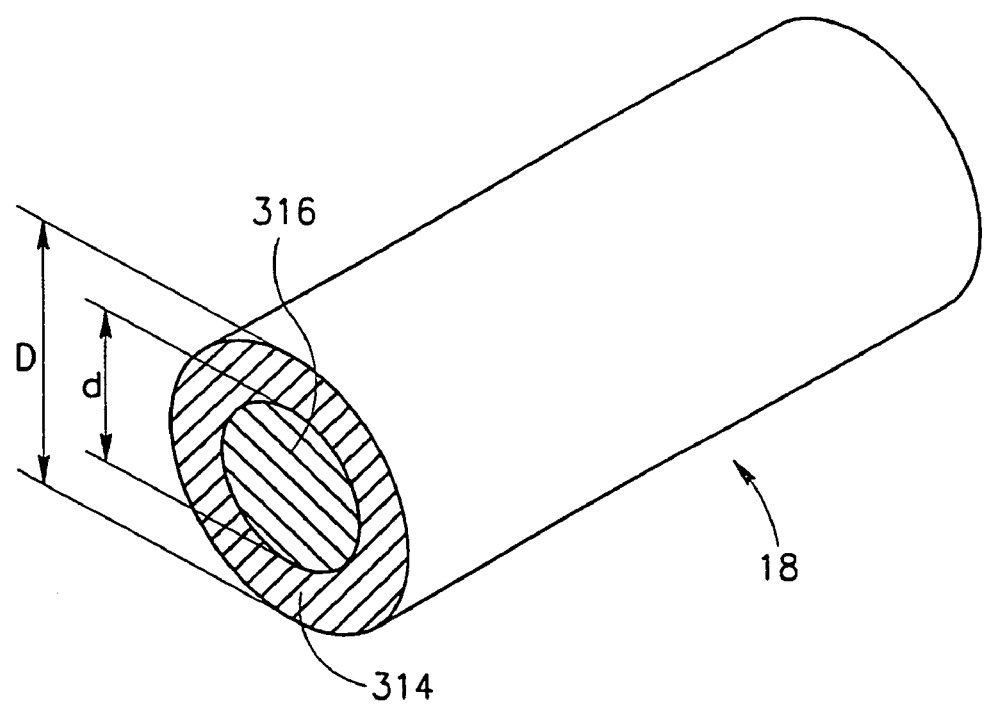

Another use of the invention is for measuring the thickness of the cortex of the bone. FIG. 12 shows bone 18 having an inner core 316 and a cortex 314. The general diameter of bone 18 is D and the diameter of inner core 316 is d. Thus, the thickness of cortex 314 is (D−d)/2.

Figure 13:
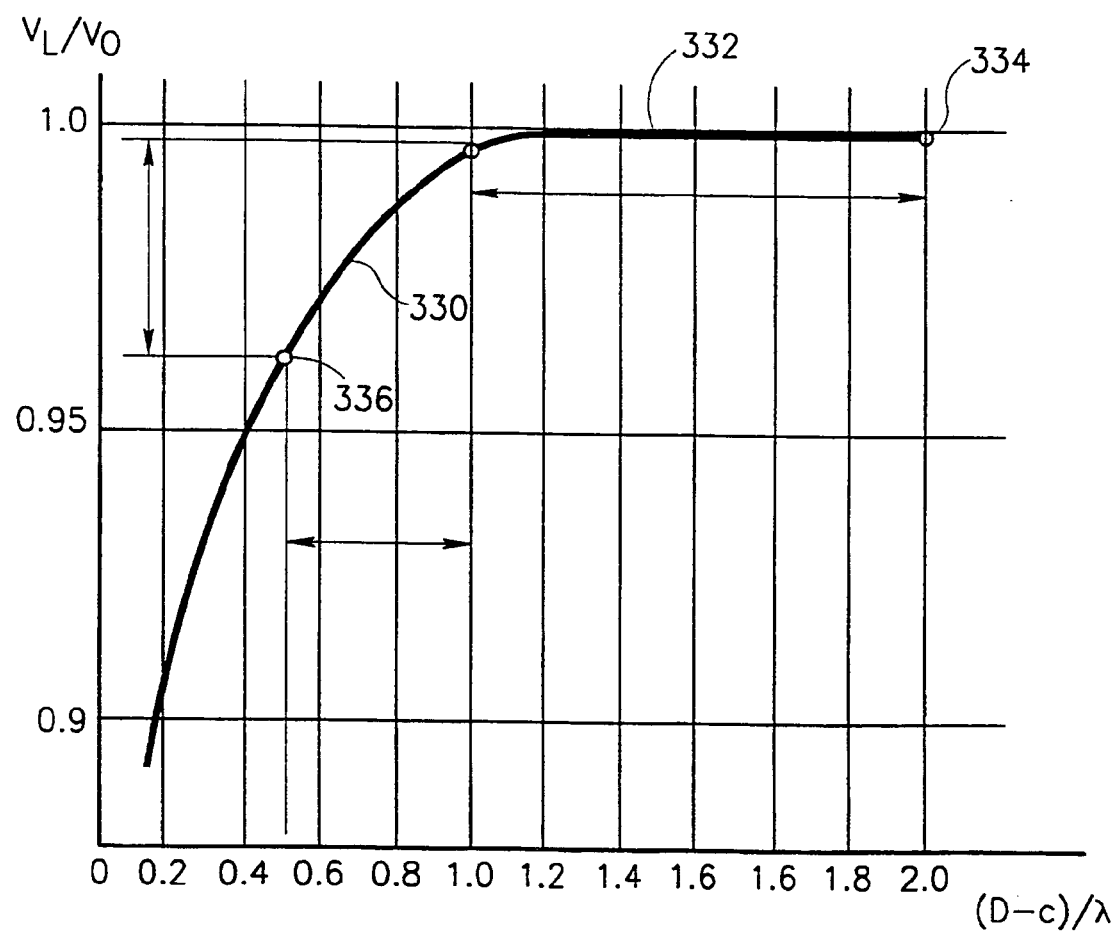
FIG. 13 is a graph showing a relationship between the thickness of an object and the velocity of an ultrasonic wave along its surface.

In accordance with a further embodiment of the present invention, computer 259 estimates the thickness of cortex 314 through utilization of an theoretically-derived and empirically-validated, non-dimensional curve of normalized velocity vs. normalized thickness, as shown in FIG. 13 to which reference is now made. A discussion of the creation of the curve in FIG. 13 is discussed in the book, *Stress Waves in Solids*, written by H. Kolsky, Oxford and Clarendon Press, 1953. Furthermore the probe 250 shown in FIGS. 1–9 can advantageously be used for these determinations.

The precise shape of the curve varies with the type of material being measured. However, it is has been determined by the present inventors that the shape of the curve is approximately constant for human bones.

The velocity $V_L$ in the curve of FIG. 13 is normalized by the velocity $V_O$ that would be achieved in an infinite solid and the thickness is normalized by the wavelength, λ, of the wave from the transmitter. λ is, of course, determined by $V_B$:

$$\lambda = V_B/f \quad (23)$$

where f is the frequency of the ultrasound wave. It has been determined by the inventors that the curve is approximately the same whether the thickness is the thickness D (FIG. 12) of bone 18 or it the thickness (D−d)/2 (FIG. 12) of cortex 314. The proposed explanation is that the when the cortex is thick relative to λ, the inner portions of the bone have no effect on the acoustic velocity. However, when the cortex is thin relative to λ, the inner portions of the bone affect the acoustic velocity. The inner portions of bones are usually much softer than the cortex, so their acoustic velocity is much lower than the cortex's acoustic velocity. Thus, if a higher frequency is used, velocity in a thinner cortex bone layer can be measured. In a preferred embodiment of the invention, the frequency used in selected to match an expected bone layer thickness. Alternatively or additionally, a filter is placed on the receiver. Alternatively or additionally, the received wave is frequency analyzed. Alternatively or additionally, several frequencies are tested to determine which frequency is most suitable. Alternatively or additionally, a broadband pulse is used and the highest suitable (which can travel through a thin cortex) frequency will general arrive first, with the lower frequencies lagging significantly behind.

It is noted that the curve has a region 330, for relatively small velocity ratios and small diameter/wavelength ratios and a region 332 for diameter/wavelength ratios greater than about 1.5 in which the ordinate is asymptotic to 1.0.

To estimate the thickness (D−d)/2 for a bone 18, the probe makes two measurements, once with a high frequency wave and once with a low frequency wave. For each measurement, computer 259 determines the wave velocity in the bone. Alternatively, in a preferred embodiment of the present invention probe 250 is a broadband probe and is operated only once. In addition, probe 250 preferably comprises frequency filters for separating received high frequency signals from low frequency signals. Thus, the high frequency velocity and the low frequency velocity are simultaneously measured utilizing the same broadband transmission.

The response to the high frequency input wave, which has a low wavelength $\lambda$, provides a velocity data point 334 somewhere along the region 332 from which the velocity $V_O$ can be determined. The precise location of data point 334 is unknown, since the thickness is not yet determined. However, its precise location is generally unimportant.

The response to the low frequency measurement provides a velocity data point 336 somewhere within the region 330. Because the velocity $V_L$ is known from the measurement and the velocity $V_O$ may be known from the previous measurement, the location on the curve of the data point 336 is known. Therefore, the ratio $(D-d)/(2*\lambda)$ can be determined. Since $\lambda$ is known from the frequency of the transmitter and the known velocities, the thickness of cortex 314 $(D-d)/2$ can be determined.

It should be appreciated that cortex thickness measurement is more practical when using the present method of acoustic bone velocity determination, than when using conventional methods. High frequency waves attenuate rapidly when traveling through bone material. So, only when the path in bone 18 is short, as is possible using the present invention, are measurements using high frequency ultrasonic waves practical. Thus, in a preferred embodiment of the invention, the high frequency wave used is higher than in the conventional devices and therefore, suitable for thinner bones.

In a preferred embodiment of the invention, probe 250 is used to determine a different one of the above four variables ($V_B$, $V_S$, $\phi$ and h), than $V_B$. In particular, it is possible to determine the velocity in soft tissue 22 using the methods and devices described herein above.

In a preferred embodiment of the invention, a soft tissue velocity measurement may be made of a tissue embedded inside a second tissue. One example of such a measurement is in determining the acoustic velocity of a suspected cancerous lump. In a preferred embodiment of the invention, soft tissue velocity is determined along two paths, one which includes the lump and one which does not. If the size of the lump is known from an imager, the acoustic velocity in the lump may be determined by assessing its effect on the average soft tissue velocity measured by the methods described herein. In a preferred embodiment of the invention, soft tissue scanning is effected using a grid type device, as described above, so that it is easy to select which path a ultrasonic pulse will travel along in the soft tissue, by varying electrification of elements, rather than by moving a probe or its elements.

In a preferred embodiment of the invention, a layer of soft tissue may be diagnosed by measuring the acoustic velocity, attenuation, frequency dependent attenuation and/or dispersion in the layer of soft tissue. Preferably, the acoustic grease used to couple the probe to the body is silicone oil having an acoustic velocity of approximately 1020 m/s. Alternatively or additionally, a grease is selected that does not fill skin pores. Alternatively or additionally, probe 250 is not pressed too hard against the soft tissue, in a manner which might compress it. By changing the frequency of the wave, and/or by transmitting a broadband pulse and determining frequency dependent responses, it is possible, according to a preferred embodiment of the present invention, to penetrate the soft tissue 22 with the wave, to a predetermined depth. As such, the velocity of the pulse in a specific layer in the soft tissue 22 (e.g., skin 20, hypodermic layer, etc.) can be determined. In general, each successive layer of skin generally has a greater thickness and a higher ultrasonic velocity than the layer above it. In a preferred embodiment of the invention, skin analysis is used for dermatology, diabetes diagnostics and/or other endocrinology uses. In a preferred embodiment of the invention, the distance between transmitters and receivers in probe 250 is decreased so that no wave travels through bone 18 faster than through the skin. Alternatively or additionally, other characteristics of probe 250 may be modified, including, pitch of ultrasonic elements and calibration settings, especially time windows for parasitic waves. These modifications are preferably made so that waves which travel along upper layers of the soft tissue are detected, while waves which travels along other paths in soft tissue and/or even in bone, are not detected or arrive outside a window of time in which soft-tissue waves are expected.

As an estimate of soft tissue layer thickness through which the fastest wave will travel, a thickness of about the wave-length $\lambda=c/f$, may be expected, where c is the ultrasound velocity in the soft tissue 22 (in m/s), and f is the frequency (in Hz). This fastest wave determines, in some preferred embodiments of the invention, the effective thickness in which a soft-tissue measurement is made. For example, when the frequency is approximately 1 MHz and the velocity in the soft tissue 22 is approximately 1500 m/s, the thickness of the layer (of the soft tissue 22) in which the measurement is made is approximately between 1.5 and 2.0 mm.

It is also possible to provide additional transmitters and/or corresponding receivers to determine velocities in different layers of the soft tissue. As described above, the velocity in the soft tissue 22 can be determined by measuring the time of a fourth pulse and solving the equations above for the velocity in the soft tissue 22. A velocity and thickness of a second soft tissue layer may be determined is two additional measurements of travel time are made. Thus, it is possible to determine the velocity of a pulse in, e.g., a layer of fat tissue and in a layer of muscle tissue.

It should be noted that many prior art methods of bone acoustic velocity determination use an inexact estimate for the values of soft tissue thickness and soft tissue velocity. If an embodiment of the present invention is used to determine more accurate values for the soft tissue thickness and velocity, these prior art methods will give more precise results.

In addition, measurement of soft tissue velocity is useful for determination of water, fat and muscle content of the tissue. Thus, dehydration and rehydration of a patient can be analyzed by measuring the soft tissue velocity, in a selected part of the patient's body, over a period of time. The muscle/fat ratio of the tissue can be determined if the water content of the tissue is known, or by averaging several results taken before and after the patient drinks water.

When scanning a human female breast, the air tissue boundary can be used as a reflection plane. Preferably the breast is urged against a resilient form so that it does not move during imaging.

In a further embodiment of the present invention, scanning is accomplished using a cell array as described hereinabove. Preferably, the scans include scans of the same soft tissue from multiple directions so that a velocity image of the tissue can be reconstructed, preferably using tomographic methods.

As described above, the arrival of a wave from the bone is usually determined by that wave being a first wave which arrives at a particular receiver. In a preferred embodiment of the invention, a first wave from a bone is detected even if it is not a first wave at the receiver. In one preferred embodiment of the invention, use is made of the fact that the wave which travels through bone has different characteristics than a wave which travels only through soft tissue and/or a wave which travels through probe 250. One example of a different characteristic frequency-dependent attenuation. Another example is frequency dependent dispersion. Thus, when a wave is detected at a receiver, that wave may be analyzed to determine when the wave changes from a "soft tissue" type wave to a "bone" type wave. Alternatively or additionally, when a wave starts arriving from the bone, an increase, in at amplitude of least certain frequency components, may be detected. Since that newly arriving wave is additive to the soft-tissue traveling wave.

In a preferred embodiment of the invention, a desired wave is detected in a method which bypasses and/or supplements the above considerations. This embodiment is based on the following observation: If a single wave is transmitted from a transmitter and is received by two different receivers, the received waves will have similar characteristics. In particular, the change in wave which occurs when a wave arrives from the bone will be similar for the two receivers, even though the background signal caused by waves which travel through soft tissue is different. In a preferred embodiment of the invention, the signal traces from two receivers are correlated to each other. It is expected that a strong correlation be detected where the bone-traveled waves arrive at the receivers. Determining a time delay by correlation may, in some cases be more accurate that first-arrived wave and may also be more robust to noise. In a preferred embodiment of the invention, the correlation is limited to a time window in which waves from the bone are expected. Alternatively or additionally, a periodic pulsed wave is used, so that the effect of a correct correlation is multiplied and can be tested against a match to the pulsing scheme.

It will be appreciated by persons skilled in the art that the present invention is not limited by what has been particularly shown and described herein. Rather, the scope of the present invention is limited only by the following claims.

The invention claimed is:

1. A method of determining an acoustic velocity in a segment of a bone covered with a layer of soft tissue having an outer surface, comprising:

determining a first travel time of a first ultrasonic wave along a first path from said outer surface back to said outer surface which path includes a first bone path in at least a first part of said bone segment and a first soft tissue path in at least part of said soft tissue;

determining a second travel time of a second ultrasonic wave along a second path from said outer surface back to said outer surface which path includes a second bone path in at least a second part of bone segment and a second soft tissue path in at least part of said soft tissue;

determining a third travel time of a third ultrasonic wave along a third path from said outer surface back to said outer surface which path includes a third bone path in at least a third part of said bone segment and a third soft tissue path in at least part of said soft tissue; and defining relationships between the acoustic velocity in bone and the travel times by a set of simultaneous equations, and deriving a value for the acoustic velocity in bone based on a solution of the set of simultaneous equations.

2. A method according to claim 1, wherein at least two of said first, second and third waves are generated simultaneously by a single transmitter.

3. A method according to claim 1, wherein at least two of said first, second and third waves are detected simultaneously by a single transmitter.

4. A method according to claim 1, wherein at least two of said first, second and third waves each have an average frequency that is substantially the same, when generated.

5. A method according to claim 1, wherein at least two of said first, second and third waves each have an average frequency that is substantially different, when generated.

6. A method according to claim 1, wherein at least two of said first, second and third waves each have an average frequency that is substantially different, when detected.

7. A method according to claim 1, wherein at least two of said first, second and third waves each have an average frequency that is substantially the same, when detected.

8. A method according to claim 1, wherein at least two of said first, second and third soft tissue paths have an overlap of at least 20%.

9. A method according to claim 1, wherein at least two of said first, second and third soft tissue paths have an overlap of at least 30%.

10. A method according to claim 1, wherein no two of said first, second and third soft tissue paths overlap by more than 20%.

11. A method according to claim 1, wherein no two of said first, second and third soft tissue paths overlap by more than 30%.

12. A method according to claim 1, wherein at least two of said first, second and third bone paths overlap at least 20% over their length.

13. A method according to claim 1, wherein at least two of said first, second and third bone paths overlap at least 40% over their length.

14. A method according to claim 1, wherein at least two of said first, second and third bone paths overlap at least 70% over their length.

15. A method according to claim 1, wherein no two of said first, second and third bone paths overlap by 20% or more of their length.

16. A method according to claim 1, wherein no two of said first, second and third bone paths overlap by 40% or more of their length.

17. A method according to claim 1, wherein no two of said first, second and third bone paths overlap by 70% or more of their length.

18. A method according to claim 1, comprising estimating a soft tissue velocity and wherein deriving said acoustic velocity comprises deriving said bone velocity using said estimated soft tissue velocity.

19. A method according to claim 1, comprising determining a fourth travel time of a fourth ultrasonic wave along a fourth path from said outer surface back to said outer surface which path includes at least a fourth part of said bone segment and wherein the set of equations comprises at least one equation defining a relationship between the acoustic velocity in bone and the fourth travel time.

20. A method according to claim 1, wherein geometric projections of at least tow of said acoustic wave paths onto the outer surface are parallel.

21. A method according to claim 1, wherein no geometric projections of said acoustic wave paths onto the outer surface are parallel to each other.

22. A method according to claim 1, wherein said acoustic waves are generated and detected by ultrasonic elements at end faces thereof and wherein said end faces are not coplanar.

23. A method according to claim 1, wherein said outer surface is not parallel to an outer surface of said bone, while said waves travel through said bone.

24. A method according to claim 1, wherein deriving comprises solving a set of simultaneous equations.

25. A method according to claim 1, comprising, repeating said determining of travel times and said deriving of acoustic velocity for a plurality of bone segments, to generate a map of acoustic bone velocity of at least a portion of a bone.

26. A method according to claim 1, comprising, repeating said determining of travel times and said deriving of acoustic velocity for a plurality of orientations of travel of said waves through said bone, to generate a map of directional acoustic bone velocity of at least a portion of a bone.

27. A method of determining at least one of a set of unknowns, including an acoustic bone velocity, acoustic soft tissue velocity, a thickness of said soft tissue and an inclination angle of an outer surface of said soft tissue relative to the bone, comprising:
   determining the travel time of at least three ultrasonic waves which travel from said surface, to said bone, along a region in said bone and back to said surface;
   assuming a value for at least one of said unknowns;
   defining relationships between the remaining unknowns by a set of simultaneous equations that are dependent on the travel times and the assumed value; and
   deriving, by solving the set of simultaneous equations, at least one of said unknowns from said three determined travel times and from said assumed value.

28. A method according to claim 27, wherein said assumed unknown comprises an acoustic soft tissue velocity.

29. A probe for acoustic bone velocity measurement, comprising:
   at least four ultrasonic elements, at least one of which comprises a transmitter and at least one of which comprises a receive; and
   a controller which controls said at least one transmitter to transmit at least three ultrasonic waves through a layer of soft tissue to a bone, which controller detects via said at least one receiver, at least relative travel times of said at least three waves, after they travel along a surface of in said bone and which controller derives an acoustic bone velocity based on a solution of a set of simultaneous equations that define relationships between the acoustic velocity in the bone and the relative travel times.

30. A probe according to claim 29, wherein said at least four ultrasonic elements comprise three transmitters and one receiver.

31. A probe according to claim 29, wherein said at least four ultrasonic elements comprise three receivers and one transmitter.

32. A probe according to claim 29, wherein said at least four ultrasonic elements comprise two receivers and two transmitters.

33. A probe according to claim 29, wherein all of said ultrasonic elements are coplanar.

34. A probe according to claim 29, wherein not all of said ultrasonic elements are coplanar.

35. A probe according to claim 29, wherein said probe comprises a surface a surface adapted to be urged against a skin layer of a soft tissue and wherein said ultrasonic elements are inclined relative to said surface of said probe at an inclination angle.

36. A probe according to claim 35, wherein said inclination angle is determined responsive to an expected acoustic bone velocity.

37. A probe according to claim 29, wherein said at least three ultrasonic waves are generated by a single transmitter as a single wave, which wave scatters to form said at least three waves.

* * * * *